United States Patent
Stancer et al.

(10) Patent No.: US 9,339,657 B2
(45) Date of Patent: May 17, 2016

(54) SELECTIVELY ENABLING A PASSIVE RECHARGE CYCLE FOR AN IMPLANTABLE CARDIAC STIMULATION DEVICE

(75) Inventors: Christopher C. Stancer, Prescott, WI (US); James J. St. Martin, Zumbrota, MN (US); Tara L. Bratten, Champlin, MN (US); Michael Hudziak, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 557 days.

(21) Appl. No.: 13/101,721

(22) Filed: May 5, 2011

(65) Prior Publication Data

US 2012/0283795 A1 Nov. 8, 2012

(51) Int. Cl.
- *A61N 1/39* (2006.01)
- *A61N 1/00* (2006.01)
- *A61N 1/37* (2006.01)
- *A61N 1/368* (2006.01)
- *A61N 1/08* (2006.01)
- *A61N 1/365* (2006.01)

(52) U.S. Cl.
CPC ............ *A61N 1/3718* (2013.01); *A61N 1/3688* (2013.01); *A61N 1/08* (2013.01); *A61N 1/36514* (2013.01); *A61N 1/36585* (2013.01); *A61N 2001/086* (2013.01)

(58) Field of Classification Search
CPC . A61N 1/36514; A61N 1/36585; A61N 1/08; A61N 2001/086; A61N 1/3718; A61N 1/3688
USPC .......................................... 607/1, 2, 4–6, 62
See application file for complete search history.

(56) References Cited

U.S. PATENT DOCUMENTS

| | | | |
|---|---|---|---|
| 3,920,024 A | 11/1975 | Bowers | |
| 4,373,531 A | 2/1983 | Wittkampf et al. | |
| 5,741,312 A | 4/1998 | Vonk et al. | |
| 5,941,903 A | 8/1999 | Zhu et al. | |
| 5,964,787 A | 10/1999 | Kerver et al. | |
| 6,067,472 A | 5/2000 | Vonk et al. | |
| 6,363,281 B1 | 3/2002 | Zhu et al. | |
| 6,516,227 B1 * | 2/2003 | Meadows et al. | 607/46 |
| 7,190,993 B2 | 3/2007 | Sharma et al. | |
| 7,454,245 B2 * | 11/2008 | Armstrong et al. | 607/2 |
| 2004/0162591 A1 * | 8/2004 | Jorgenson et al. | 607/27 |
| 2009/0138058 A1 * | 5/2009 | Cooke et al. | 607/5 |
| 2011/0160803 A1 * | 6/2011 | Stessman et al. | 607/62 |

* cited by examiner

*Primary Examiner* — Niketa Patel
*Assistant Examiner* — Lindsey G Hankins
(74) *Attorney, Agent, or Firm* — Michael J. Ostrom

(57) ABSTRACT

Techniques are described for selectively enabling and disabling a pre-stimulation passive recharge pacing mode for an implantable medical device (IMD) depending on whether the IMD is operating in an electromagnetic interference (EMI)-safe mode. In some examples, the IMD may enable the pre-stimulation passive recharge pacing mode when the IMD is operating in the EMI-safe mode, and disable the pre-stimulation passive recharge pacing mode when the IMD is not operating in the EMI-safe mode. The EMI-safe mode may be, in some examples, a magnetic resonance imaging (MRI)-safe mode.

26 Claims, 9 Drawing Sheets

SELECTIVELY ENABLING A PASSIVE RECHARGE CYCLE FOR AN IMPLANTABLE CARDIAC STIMULATION DEVICE

TECHNICAL FIELD

The disclosure relates to implantable medical devices (IMDs), and more particularly, to implantable stimulation devices.

BACKGROUND

An implantable medical device (IMD) may be exposed to electromagnetic interference (EMI) for any of a number of reasons. For example, certain types of medical procedures may need to be performed on a patient within whom the IMD is implanted for purposes of diagnostics or therapy. A patient carrying an implanted IMD may need, for example, to have a magnetic resonance imaging (MRI) scan, a computed tomography (CT) scan, an electrocautery procedure, a diathermy procedure or another type of medical procedure that produces a magnetic field, an electromagnetic field, an electric field or other type of electromagnetic energy. The electromagnetic energy produced by such medical procedures may interfere with the operation of the IMD. For example, the electromagnetic energy may rectify within the IMD, which may interfere with the operation of the internal circuitry of the IMD and/or alter the delivery of therapy by the IMD.

SUMMARY

This disclosure describes techniques for selectively enabling and disabling a pre-stimulation passive recharge pacing mode for an implantable medical device (IMD) depending on whether the IMD is operating in an electromagnetic interference (EMI)-safe mode. In an EMI-safe mode, the IMD may enable a pre-stimulation passive recharge pacing mode that includes a pre-stimulation passive recharge cycle. In a normal mode, the IMD may enable a normal pacing mode that does not include the pre-stimulation passive recharge cycle.

In one aspect, this disclosure is directed to a method that includes selectively enabling and disabling, with a control module within an implantable medical device (IMD), a pre-stimulation passive recharge pacing mode for the IMD based on whether the IMD is operating in an electromagnetic interference (EMI)-safe mode.

In another aspect, this disclosure is directed to an IMD that includes a pacing mode selection module configured to selectively enable and disable a pre-stimulation passive recharge pacing mode for the IMD based on whether the IMD is operating in an electromagnetic interference (EMI)-safe mode.

In another aspect, this disclosure is directed to an apparatus that includes pacing means for delivering pacing therapy to cardiac tissue; and means for selectively enabling and disabling a pre-stimulation passive recharge pacing mode for the pacing means based on whether the pacing means is operating in an electromagnetic interference (EMI)-safe mode.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
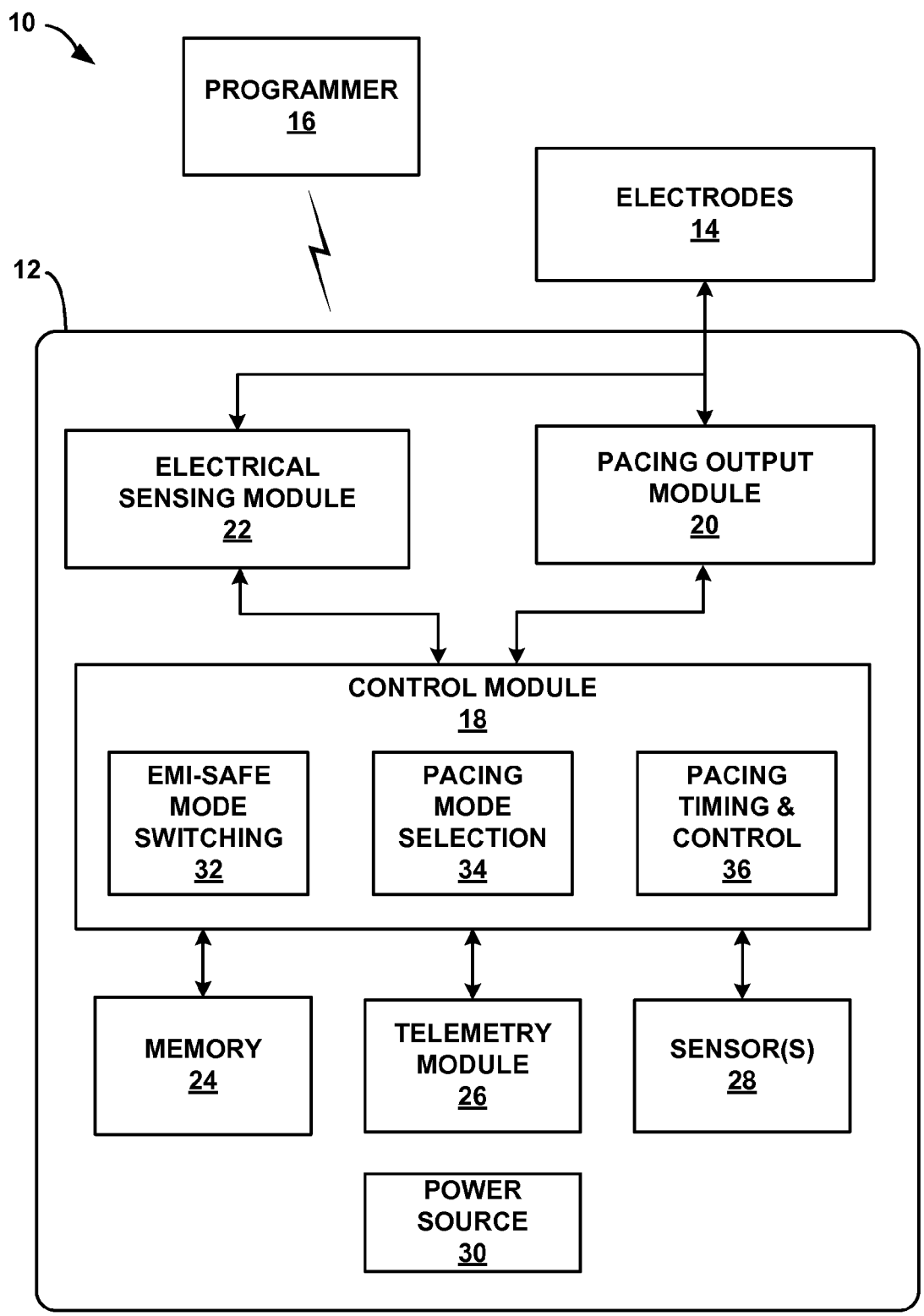
FIG. 1 is a block diagram illustrating an example therapy system that implements the selective pre-stimulation passive recharge pacing techniques according to this disclosure.

This disclosure describes techniques for selectively enabling and disabling a pre-stimulation passive recharge pacing mode for an implantable medical device (IMD) depending on whether the IMD is operating in an electromagnetic interference (EMI)-safe mode. The pre-stimulation passive recharge pacing mode may be more resilient to EMI than a normal pacing mode for the IMD. However, the pre-stimulation passive recharge pacing mode may consume more power than the normal pacing mode and/or preclude certain IMD functionality from being performed that is otherwise capable of being performed in the normal pacing mode. Therefore, by selectively enabling and disabling the pre-stimulation passive recharge pacing mode according to the techniques of this disclosure, an IMD may deliver a more resilient pacing therapy when the IMD is subject to an interfering EMI source without necessarily needing to sacrifice power consumption and/or other functionality of the IMD when the IMD is not subject to the interfering EMI source.

When an IMD designed in accordance with this disclosure is operating in the EMI-safe mode, the IMD may enable the pre-stimulation passive recharge pacing mode in order to perform a pre-stimulation passive recharge cycle prior to the delivery of a pacing pulse. The pre-stimulation passive recharge cycle may discharge one or more coupling capacitors within the IMD prior to delivering a pacing pulse. As used herein, a passive recharge cycle may refer to the discharging of one or more coupling capacitors without actively driving a current through the coupling capacitor. In contrast, an active recharge cycle may actively drive a current through the coupling capacitor to discharge the coupling capacitor. EMI energy incident upon the IMD may induce an electrical charge across the one or more coupling capacitors, which may interfere with the pacing operations of the IMD. For example, EMI-induced charge across the coupling capacitors may alter the magnitude of the pacing pulse, which may cause overstimulation, understimulation or affect the pacing capture threshold, i.e., the amount of voltage that needs to be produced by a pulse generator to cause a depolarization of the heart. The pre-stimulation passive recharge cycle, however, reduces and/or eliminates the EMI-induced charge across the coupling capacitor prior to the delivery of a pacing pulse. Thus, by enabling a pre-stimulation passive recharge pacing mode when the IMD is operating in the EMI-safe mode, the IMD is able to mitigate the effects caused by EMI-induced charges on the coupling capacitors within the IMD, thereby providing pacing therapy that is more resilient to EMI when the IMD is subject to EMI.

When the IMD is not operating in the EMI-safe mode, the IMD may disable the pre-stimulation passive recharge pacing mode. Disabling the pre-stimulation passive recharge pacing mode when the IMD is not operating in the EMI-safe mode may provide one or more advantages. As one example, the pre-stimulation passive recharge pacing mode may, in some embodiments, consume more power than the normal pacing mode. Thus, disabling the pre-stimulation passive recharge pacing mode in such embodiments may reduce the power consumption of the IMD. As another example, in some embodiments, one or more functionalities of the IMD may not be able to be performed when the pre-stimulation passive recharge pacing mode is enabled. For example, the IMD may not be able to perform lead impedance testing when the pre-stimulation passive recharge pacing mode is enabled and/or the IMD may not be able to sense one or more cardiac signals in order to, e.g., deliver demand pacing therapy when the pre-stimulation passive recharge pacing mode is enabled. Therefore, by disabling the pre-stimulation passive recharge pacing mode in such embodiments, the IMD may be able to perform functionalities that would otherwise not be able to be performed if the pre-stimulation passive recharge were enabled one hundred percent of the time.

In some examples, the EMI-safe mode may be a magnetic resonance imaging (MRI)-safe mode. One of the concerns associated with the delivery of pacing therapy during MRI scans is that MRI radio-frequency (RF) voltage induced in a device lead or entering the telemetry antenna can rectify inside the IMD. Between pacing pulses, the rectified signal may charge up a coupling capacitor disposed between the holding capacitor and the pacing electrode, e.g., a tip capacitor, and then cause the amplitude of the pacing pulse to be shifted and/or offset by the direct current (DC) voltage on the tip capacitor. This pacing pulse shift may be positive or negative. In other words, the shift in the pacing pulse amplitude may add to or subtract from the delivered pacing energy, which could impact the pacing capture threshold. The pre-stimulation passive recharge pacing mode described in this disclosure may discharge the tip pacing capacitor prior to delivering a pacing pulse. Therefore, by selectively enabling the pre-stimulation passive recharge pacing mode according to the techniques of this disclosure, the effects due to MRI-induced charge build-up on the coupling capacitor may be mitigated when a patient is undergoing an MRI scan while not disrupting the normal operation of the IMD when the patient is not undergoing an MRI scan.

In further examples, when the IMD is operating in the EMI-safe mode, the IMD may be configured to pace according to an asynchronous pacing mode that does not rely upon sensed cardiac activity for the delivery of pacing therapy. When the IMD is not operating in the EMI-safe mode, the IMD may be configured to pace according to a demand pacing mode that relies upon sensed cardiac activity, e.g., a pacing mode that triggers or inhibits pacing therapy in response to sensed cardiac activity. When pacing according to the demand pacing mode, the IMD may sense cardiac activity using one or more electrodes through which demand pacing therapy is also delivered. The IMD may enable the asynchronous pacing mode when operating in the EMI-safe mode because EMI may interfere with the accurate sensing of cardiac events, thereby also interfering with the delivery of demand pacing therapy. The pre-stimulation passive recharge cycles described in this disclosure may also interfere with the sensing of cardiac events. However, because the demand pacing mode is already disabled when the IMD is operating in the EMI-safe mode, in such examples, cardiac sensing may not be needed to provide pacing therapy. Therefore, by enabling the pre-stimulation passive recharge pacing mode when operating in the EMI-safe mode, the IMD may perform pre-stimulation passive recharge cycles without the concern of interfering with cardiac sensing needed to provide demand pacing therapy. Moreover, by disabling the pre-stimulation passive recharge pacing mode when not operating in the EMI-safe mode, the IMD may be able to deliver demand pacing therapy when the passive recharge pacing mode is not needed and without concern of interference in cardiac sensing by the pre-stimulation passive recharge cycles. Therefore, by selectively enabling and disabling the pre-stimulation passive recharge pacing mode according to the techniques of this disclosure, the IMD may be able to obtain the benefits of a pacing therapy that is more robust to EMI when the IMD is being subjected to EMI, and demand pacing is consequently disabled, while not interfering with the delivery of demand pacing therapy when the IMD is not being subjected to EMI.

Some IMDs may perform a post-stimulation passive recharge cycle immediately after delivering a pacing pulse. Such a passive recharge cycle is typically done to clear out any residual tip capacitor charge that is left over from the pacing energy, e.g., a residual polarization voltage or after-potential that occurs following the delivery of a pacing pulse. The post-stimulation passive recharge cycle typically ends well before the next pacing pulse within a pacing cycle in order to allow for other functionality to take place, for example, R-wave sensing to confirm capture. Although the post-stimulation passive recharge cycle may be capable of discharging EMI-induced charge immediately after the delivery of a pacing pulse, the post-stimulation passive recharge cycle does not compensate for EMI-induced charge that may build up after completion of the recharge cycle and prior to the delivery of the next pacing pulse. The pre-stimulation passive recharge pacing mode described in this disclosure, however, may be configured to perform a pre-stimulation passive recharge cycle in order to compensate for EMI-induced charge that occurs after completion of a post-stimulation passive recharge pacing mode, thereby overcoming the deficiencies in performing merely a post-stimulation passive recharge cycle alone.

FIG. 1 is a block diagram illustrating an example therapy system 10 that implements the selective pre-stimulation passive recharge pacing techniques according to this disclosure. Therapy system 10 is configured to monitor one or more physiological parameters of a patient and/or provide therapy to the heart of a patient. Therapy system 10 includes an implantable medical device (IMD) 12, electrodes 14 and a programmer 16.

IMD 12 is configured to provide electrical stimulation via electrodes 14 to provide therapy, e.g., pacing therapy, to cardiac tissue within a patient. IMD 12 may also be configured to sense one or more electrical signals via electrodes 14. In some examples, IMD 12 may use the one or more sensed electrical signals to control timing parameters and/or other parameters associated with the delivery of pacing therapy. IMD 12 may also be configured to communicate with one or more external devices, e.g., via a telemetry system.

IMD 12 may be, for example, an implantable pacemaker, a cardioverter that provides pacing therapy and cardioversion shocks, a defibrillator that provides pacing therapy and defibrillation shocks, a combined cardioverter-defibrillator, or any other implantable device that delivers pacing therapy to the heart of a patient. In some examples, IMD 12 may be a lead-based pacing device, e.g., a lead-based pacemaker, that includes one or more leads that carry electrodes 14. In further examples, IMD 12 may be a leadless pacing device, e.g., a leadless pacemaker that does not include leads that carry electrodes 14. IMD 12 includes a control module 18, a pacing output module 20, an electrical sensing module 22, a memory 24, a telemetry module 26, sensors 28 and a power source 30.

Control module 18 is configured to control the operation of IMD 12 and to interact with the other components of IMD 12. For example, control module 18 may control pacing output module 20 to provide appropriate pacing therapy to a patient. As another example, control module 18 may control electrical sensing module 22 to receive particular electrical signals indicative of cardiac activity and, in some examples, to perform a particular signal processing technique on the sensed signals. As an additional example, control module 18 may manage the storage and retrieval of data and/or program instructions within memory 24. As a further example, control module 18 may coordinate communications with external devices via telemetry module 26. As another example, control module 18, may manage the operation of and/or retrieve sensing data from sensors 28. As yet another example, control module 18 may perform one or more lead impedance tests. Control module 18 may include an electromagnetic interference (EMI)-safe mode switching module 32, a pacing mode selection module 34 and a pacing timing and control module 36.

Control module 18 may include one or more of a microprocessor, a controller, a digital signal processor (DSP), an application specific integrated circuit (ASIC), a field-programmable gate array (FPGA), as well as other equivalent discrete or integrated logic circuitry. In some examples, control module 18 may include multiple components, such as any combination of one or more microprocessors, one or more controllers, one or more DSPs, one or more ASICs, or one or more FPGAs, as well as other discrete or integrated logic circuitry. The functions attributed to control module 18 herein may be embodied as software, firmware, hardware or any combination thereof. In some examples, control module 18 and/or memory 24 may include a computer-readable medium comprising instructions that cause one or more programmable processor to perform the techniques described in this disclosure.

EMI-safe mode switching module 32 is configured to control the current operational mode of IMD 12. For example, EMI-safe mode switching module 32 may switch the current operational mode of IMD 12 between a normal mode and an EMI-safe mode. In some examples, the EMI-safe mode may be a magnetic resonance imaging (MRI)-safe mode.

In a first example, EMI-safe mode switching module 32 may receive one or more commands from an external device that instruct IMD 12 to switch the current operational mode of IMD 12. For example, EMI-safe mode switching module 32 may receive a command that instructs IMD 12 to switch into an EMI-safe operational mode and/or a command that instructs IMD 12 to switch into the normal operational mode. EMI-safe mode switching module 32 may then control the current operational mode of IMD 12 based on the received commands. For example, EMI-safe mode switching module 32 may switch IMD 12 from a normal node into an EMI-safe mode in response to receiving a command instructing IMD 12 to switch into the EMI-safe mode, and switch IMD 12 from the EMI-safe mode into the normal operational mode in response to receiving a command instructing IMD 12 to switch to the normal operational mode.

In some implementations of the first example, the external device may be a programmer 16, and EMI-safe mode switching module 32 may receive the commands from programmer 16, via telemetry module 26. For example, a patient or clinician may enter mode instructions into programmer 16 that are transmitted to EMI-safe mode switching module 32 of IMD 12. In additional implementations of the first example, the external device may be an external magnet that actuates a reed switch (not shown) or a hall sensor (not shown) within IMD12, and EMI-safe mode switching module 32 may receive the commands from a reed switch interface (not shown) or a hall sensor interface (not shown). In such implementations, the EMI-safe mode may be referred as a magnet mode for the IMD. In general, programmer 16 may receive the commands from any type of external device via any type of communication interface between the external device and IMD 12.

In a second example, EMI-safe mode switching module 32 may receive sensing information from one or more of sensors 28, and determine whether IMD 12 is being subjected to EMI having one or more particular characteristics based on the sensing information. EMI-safe mode switching module 32 may then control the current operational mode of IMD 12 based on the sensing information. For example, EMI-safe mode switching module 32 may switch IMD 12 from a normal node into an EMI-safe mode in response to determining that IMD 12 is being subjected to the EMI having the one or more particular characteristics, and switch IMD 12 from the EMI-safe mode into the normal operational mode in response to determining that IMD 12 is not being subjected to the EMI having the one or more particular characteristics. Determining whether IMD 12 is being subjected to EMI having one or more particular characteristics may, in some examples, include determining whether IMD 12 is being subjected to EMI of a particular type, e.g., MRI energy, or energy due to electrocautery procedures, external defibrillation, radio-frequency (RF) ablation, radio-frequency identification (RFID) readers, airport scanners, large RF sources, or any other particular type of EMI energy. EMI-safe mode switching module 32 may determine that IMD 12 is being subjected to EMI energy having one or more characteristics and/or to MRI energy using any of a variety of automated EMI sensing techniques known in the art.

In some implementations of the second example, EMI-safe mode switching module 32 may determine whether IMD 12 is being subjected to MRI energy generated by an MRI scanning device. The MRI energy may include, e.g., static magnetic fields, magnetic field gradients and/or electromagnetic fields. In such implementations, EMI-safe mode switching module 32 may switch IMD 12 from a normal operational mode into an MRI-safe mode in response to determining that IMD 12 is being subjected to MRI energy, and switch IMD 12 from the MRI-safe mode into the normal operational mode in response to determining that IMD 12 is not being subjected to MRI energy.

In some examples, EMI-safe mode switching module 32 may be configured to provide the current operational mode of IMD 12, e.g., EMI-safe mode or normal mode, to other components within control module 18, such as, e.g., pacing mode selection module 34 and/or pacing timing and control module 36. In additional examples, EMI-safe mode switching module 32 may be configured to store the current operational mode of IMD 12 within memory 24 from which other components may access the operational state.

According to this disclosure, pacing mode selection module 34 is configured to selectively enable and disable a pre-stimulation passive recharge pacing mode based on whether IMD 12 is operating in the EMI-safe mode. For example, pacing mode selection module 34 may enable the pre-stimulation passive recharge pacing mode when IMD 12 is operating in the EMI-safe mode, and disable the pre-stimulation passive recharge pacing mode when the IMD is not operating in the EMI-safe mode. The pre-stimulation passive recharge pacing mode may be more resilient to EMI than pacing according to a normal pacing mode. However, the pre-stimulation passive recharge pacing mode may consume more power than the normal pacing mode and/or preclude certain IMD functionality from being performed that is otherwise capable of being performed in the normal pacing mode. Therefore, by selectively enabling and disabling the pre-stimulation passive recharge pacing mode, the techniques in this disclosure may allow an IMD to deliver a more resilient pacing therapy when the IMD is subject to an interfering EMI source without necessarily needing to sacrifice power consumption and/or other functionality of the IMD when the IMD is not subject to the interfering EMI source.

In addition to selectively enabling and disabling the pre-stimulation passive recharge pacing pulse, pacing mode selection module 34 may also selectively enable and disable a lead impedance testing based on whether IMD 12 is operating in the EMI-safe mode. For example, pacing mode selection module 34 may enable lead impedance testing when the IMD is not operating in the EMI-safe mode, and disable lead impedance testing when the IMD is operating in the EMI-safe mode. IMD 12 may perform lead impedance testing, e.g., to determine the lead integrity of one or more leads that deliver pacing therapy. For example, lead impedance testing may be used to detect a fractured lead and/or a shorted lead. The pre-stimulation passive recharge cycle described in this disclosure may interfere with a lead impedance test that occurs during the same time frame as the pre-stimulation passive recharge cycle. Therefore, by disabling lead impedance testing when pacing in the pre-stimulation passive recharge mode, and enabling lead impedance testing when not pacing in the pre-stimulation passive recharge mode, the EMI-robust benefits of the pre-stimulation passive recharge pacing mode may be obtained when needed without withholding the performance of lead impedance tests at times when the pre-stimulation passive recharge pacing mode is not needed.

In additional examples, pacing mode selection module 34 may also selectively enable and disable an asynchronous pacing mode and/or a demand pacing mode based on whether IMD 12 is operating in the EMI-safe mode. For example, pacing mode selection module 34 may disable the demand pacing mode, i.e., enable the asynchronous pacing mode, when IMD 12 is operating in the EMI-safe mode. Similarly, pacing mode selection module 34 may enable the demand pacing mode, i.e., disable the asynchronous pacing mode, when IMD 12 is not operating in the EMI-safe mode. When pacing according to the demand pacing mode, IMD 12 may sense cardiac activity using one or more electrodes through which demand pacing therapy is also delivered. Pacing mode selection module 34 may enable the asynchronous pacing mode when operating in the EMI-safe mode because EMI may interfere with the accurate sensing of cardiac events, thereby also interfering with the delivery of demand pacing therapy. The pre-stimulation passive recharge cycles described in this disclosure may also interfere with the sensing of electrical cardiac activity. However, because the demand pacing mode is already disabled when IMD 12 is operating in the EMI-safe mode, in such examples, cardiac sensing may not be needed to provide pacing therapy. Therefore, by enabling the pre-stimulation passive recharge pacing mode when operating in the EMI-safe mode, IMD 12 may perform pre-stimulation passive recharge cycles without the concern of interfering with cardiac sensing needed to provide demand pacing therapy. Moreover, by disabling the pre-stimulation passive recharge pacing mode when not operating in the EMI-safe mode, IMD 12 may be able to deliver demand pacing therapy when the passive recharge pacing mode is not needed and without concern of interference in cardiac sensing by the pre-stimulation passive recharge cycles. Therefore, by selectively enabling and disabling the pre-stimulation passive recharge pacing mode according to the techniques of this disclosure, IMD 12 may be able to obtain the benefits of a pacing therapy that is more robust to EMI when IMD 12 is being subjected to EMI, and demand pacing is consequently disabled, while not interfering with the delivery of demand pacing therapy when IMD 12 is not being subjected to EMI.

Pacing mode selection module 34 may receive current operational mode information from EMI-safe mode switching module 32 and/or from memory 24, and enable or disable the pre-stimulation passive recharge pacing mode based on the current operational mode information. In some examples, pacing mode selection module 34 may enable and/or disable the pre-stimulation passive recharge pacing mode by providing one or more control signals to pacing timing and control module 36. The control signals may instruct pacing timing and control module 36 to enable or disable the pre-stimulation passive recharge pacing mode. In additional examples, pacing mode selection module 34 may enable and/or disable the pre-stimulation passive recharge pacing mode by providing a signal indicative of the current pacing mode, e.g., pre-stimulation passive recharge pacing mode or normal pacing mode, to pacing timing and control module 36. In additional examples, pacing mode selection module 34 may enable and/or disable the pre-stimulation passive recharge pacing mode by storing the current pacing mode within memory 24 from which pacing timing and control module 36 may access the current pacing mode.

Pacing timing and control module 36 is configured to coordinate the timing of and control the delivery of pacing therapy to cardiac tissue within the patient. Pacing timing and control module 36 may deliver pacing therapy according to a normal pacing mode and a pre-stimulation passive recharge pacing mode depending on whether the pre-stimulation passive recharge pacing mode is enabled or disabled.

Pacing timing and control module 36 may control the operation of pacing output module 20 in order to deliver the appropriate pacing therapy. For example, when the pre-stimulation passive recharge pacing mode is enabled, pacing timing and control module 36 may control pacing output module 20 to deliver pacing therapy that includes a pre-stimulation passive recharge cycle. On the contrary, when the pre-stimulation passive recharge pacing mode is disabled, pacing timing and control module 36 may control pacing output module 20 to deliver pacing therapy that does not include a pre-stimulation passive recharge cycle.

In some examples, when the pre-stimulation passive recharge pacing mode is enabled, pacing timing and control module 36 may control pacing output module 20 to perform both a pre-stimulation passive recharge cycle and a post-stimulation passive recharge cycle. Thus, in such examples, pacing timing and control module 36 may perform at least two different passive recharge cycles between two consecutive pacing pulses. For example, pacing timing and control module 36 may control pacing output module 20 to deliver a first pacing pulse, to perform a post-stimulation passive recharge cycle after delivering the pacing pulse, and to perform a pre-stimulation passive recharge cycle after performing the post-stimulation passive recharge cycle and prior to delivery of a subsequent pacing pulse. The subsequent pacing pulse may be a next sequential pacing pulse that occurs after the first pacing pulse. In other examples, when the pre-stimulation passive recharge pacing mode is enabled, pacing timing and control module 36 may control pacing output module 20 to perform the pre-stimulation passive recharge cycle without necessarily performing a post-stimulation passive recharge cycle prior to the pre-stimulation passive recharge cycle.

In further examples, when the pre-stimulation passive recharge pacing mode is disabled, pacing timing and control module 36 may control pacing output module 20 to perform a post-stimulation passive recharge cycle. For example, pacing timing and control module 36 may control pacing output module 20 to deliver a first pacing pulse, to perform a post-stimulation passive recharge cycle after delivering the pacing pulse, and to deliver a subsequent pacing pulse after performing the passive recharge cycle without performing any intervening passive recharge cycles in between the post-stimulation passive recharge cycle and the subsequent pacing pulse. The subsequent pacing pulse may be a next sequential pacing pulse that occurs after the first pacing pulse. In other examples, when the pre-stimulation passive recharge pacing mode is disabled, pacing timing and control module 36 may control pacing output module 20 to deliver consecutive pacing pulses without performing any intervening passive recharge cycles at all.

Pacing timing and control module 36 may, in some examples, deliver a pacing pulse by placing pacing output module 20 into a pacing configuration, and perform passive recharge cycles by placing pacing output module 20 into a passive recharge configuration. When the pre-stimulation passive recharge pacing mode is enabled, pacing timing and control module 36 may configure pacing output module 20 into a passive recharge configuration prior to delivering a pacing pulse in order to perform a pre-stimulation passive recharge cycle. The passive recharge configuration may discharge a coupling capacitor in pacing output module 20 for a particular amount of time. After the time frame for the passive recharge cycle has expired, pacing timing and control module 36 may configure pacing output module 20 into a pacing configuration to deliver a pacing pulse. The pacing configuration may transfer energy from a holding capacitor, through the coupling capacitor and through an electrode to cardiac tissue within the patient. After delivering the pacing pulse, pacing timing and control module 36 may again place pacing output module 20 into a passive recharge configuration to perform a post-stimulation passive recharge cycle. The configuration used by pacing output module 20 to perform the pre-stimulation passive recharge cycle may be, in some examples, the same configuration that is used to perform the post-stimulation passive recharge cycle. Some implementations may omit the post-stimulation passive recharge cycle. Between paces, pacing timing and control module 36 may also place pacing output module 20 into a charging configuration to recharge the holding capacitor. The time frame for recharging the holding capacitor may or may not overlap with the time frames allotted for performing the passive recharge cycles. In some implementations, pacing timing and control module 36 may change the configuration of pacing output module 20 at least in part by controlling the operations of one or more switches in pacing output module 20 which will be described in further detail below. When the pre-stimulation passive recharge pacing mode is disabled, pacing timing and control module 36 may operate in a similar manner except that the pre-stimulation passive recharge cycle is omitted.

Pacing timing and control module 36 may control pacing output module 20 to deliver any type of pacing therapy according to a variety of pacing techniques. For example, pacing timing and control module 36 may control pacing output module 20 to deliver asynchronous pacing therapy, demand pacing therapy and/or rate-responsive pacing therapy. Pacing timing and control module 36 may deliver, for example, single-chamber pacing therapy, dual chamber pacing therapy, atrial pacing therapy, ventricular pacing therapy, bi-ventricular pacing therapy and/or multi-site pacing therapy. In some examples, pacing timing and control module 36 may control pacing output module 20 to deliver pacing therapy in accordance with one or more of the Heart Rhythm Society and the British Pacing and Electrophysiology Group (BPEG) pacing modes.

Pacing timing and control module 36 may use one or more timers and/or sensed events to control pacing output module 20 for the delivery of pacing therapy. For example, pacing timing and control module 36 may trigger pacing output module 20 to deliver pacing therapy based on the expiration of a timer and/or the occurrence of a sensed event. As another example, pacing timing and control module 36 may trigger pacing output module 20 to inhibit pacing therapy based on the expiration of a timer or the occurrence of a sensed event. In additional examples, pacing timing and control module 36 may use sensing information from one or more of sensors 28 to control the delivery of pacing pulses. For example, pacing timing and control module 36 may use sensed physiologic information to control the pacing rate.

It should be noted that the normal pacing mode and the pre-stimulation passive recharge pacing mode described in this disclosure are two pacing modes that define one particular aspect or parameter for a cardiac pacing technique, namely, whether or not a pre-stimulation passive recharge cycle will be performed. The two pacing modes described in this disclosure may be combined with other pacing techniques and parameters to specify an overall pacing technique. For example, the techniques of this disclosure may be combined with and/or compatible with the independent selection of other pacing parameters that specify, for example, which chambers of the heart are paced and/or how a pacing cycle is either triggered or inhibited.

Pacing output module 20 is configured to receive configuration information and timing information from pacing timing and control module 36 and to deliver pacing pulses to cardiac tissue via electrodes 14. Pacing output module 20 may be switchable between a pacing configuration and a passive recharge configuration based on configuration information provided by pacing timing and control module 36. In some examples, pacing output module 20 may include a coupling capacitor in the pacing circuit path. When pacing output module 20 is in the pacing configuration, the coupling capacitor may allow the pacing pulse to travel through the cardiac tissue, but block direct current (DC) components from travelling through the cardiac tissue. When pacing output module 20 is in a passive recharge state, pacing output module 20 may discharge the coupling capacitor. As discussed above, EMI energy, such as MRI energy for example, may cause a charge build-up to occur on the coupling capacitor between the delivery of pacing pulses. This charge build-up may shift the amplitude of a delivered pacing pulse, which may lead to overstimulation or understimulation. According to this disclosure, pacing timing and control module 36 may place pacing output module 20 into the passive recharge configuration soon before or immediately prior to the delivery of a pacing pulse in order to reduce or remove the EMI-induced charge build-up.

In some examples, pacing timing and control module 36 may also place pacing output module 20 into a passive recharge cycle soon after or immediately after the delivery of a pacing pulse in order to perform a post-stimulation passive recharge cycle. The post-stimulation passive recharge cycle may reduce or remove charge build-up on the coupling capacitor that is due to one or both of EMI and pacing after-potential.

Pacing output module 20 may also be configured to charge up a holding capacitor in order to prepare for the delivery of a pacing pulse. The holding capacitor charging cycle may or may not overlap with one or more of the passive recharge cycles.

Electrical sensing module 22 is configured to sense electrical signals indicative of cardiac activity via electrodes 14, to optionally perform processing on the sensed signals, and to deliver the processed sensed signals to control module 18 for further processing. Electrical sensing module 22 may include signal processing circuitry such as, e.g., bandpass filters, sense amplifiers, blanking circuitry, analog-to-digital converters and/or detection circuits. In some examples, electrical sensing module 22 may detect the presence of an R-wave in a sensed electrical signal received from one or more of electrodes 14 and provide an R-wave sensed event indicator to control module 18 for further processing. In further examples, electrical sensing module 22 may detect the presence of a P-wave in a sensed electrical signal received from one or more of electrodes 14 and provide a P-wave sensed event indicator to control module 18 for further processing. Control module 18 may use the P-wave and R-wave sensed event indicators and/or any other processed signals from electrical sensing module 22 to adjust the pacing therapy delivered to the cardiac tissue by pacing output module 20. In some examples, control module 18 may save the sensed signals in memory 24, e.g., as an intracardiac electrogram (EGM).

Memory 24 is configured to store program instructions, pacing therapy parameters, sensed data information and/or device status information. In some examples, memory 24 may store information indicative of whether IMD 12 is currently operating in an EMI-safe mode. For example, IMD 12 may store the current operational mode for IMD 12, e.g., normal mode vs. EMI-safe mode. The information indicative of whether IMD 12 is currently operating in an EMI-safe mode may be retrieved by pacing mode selection module 34 and used to select a pacing mode for IMD 12. In additional examples, memory 24 may store the current pacing mode for IMD 12, e.g., normal pacing mode vs. pre-stimulation passive recharge pacing mode. The current pacing mode stored in memory 24 may be retrieved by pacing timing and control module 36 and used to control the delivery of pacing therapy by IMD 12. Memory 24 may include one or more volatile or non-volatile memories or storage devices, such as, for example, random access memory (RAM), static RAM (SRAM), dynamic RAM (DRAM), read-only memory (ROM), erasable programmable ROM (EPROM), electrically erasable programmable ROM (EEPROM), Flash memory, magnetic data media or optical storage media.

Telemetry module 26 provides a communications interface between IMD 12 and one or more other devices external to the patient and/or implanted within the patient. For example, telemetry module 26 may provide a wireless communication interface between IMD 12 and programmer 16. In such an example, control module 18 may provide data to telemetry module 26 to send via uplink telemetry to programmer 16, and telemetry module 26 may receive downlink telemetry from programmer 16 and provide the data to control module 18. In some examples, telemetry module 26 may receive one or more commands from programmer 16 instructing IMD 12 to switch between a normal mode and an EMI-safe mode, e.g., an MRI-safe mode. Telemetry module 26 may also exchange other data with one or more external devices including, for example, physiological data acquired by IMD 12, information related to therapies delivered by IMD 12 and information related to the operational status of IMD 12. Telemetry module 26 may include any suitable hardware, firmware, software or any combination thereof for communicating with another device. Telemetry module 26 may utilize one or more telemetry antennas and one or both of near-field and far-field telemetry techniques to facilitate wireless communication between IMD 12 and the other devices.

Sensors 28 include one or more sensors that may provide sensing information to control module 18. In some examples, the sensing information may be used by EMI-safe mode switching module 32 as part of an automatic EMI-detection technique. For example, control module 18 may use the sensing information provided by sensors 28 alone or in conjunction with other information to determine whether IMD 12 is being subjected to EMI having one or more particular characteristics. As a specific example, control module 18 may use the sensing information provided by sensors 28 to determine whether IMD 12 is being subjected to MRI energy. Sensors 28 may be any type of sensor that provides information indicative of EMI and/or MRI energy in the surrounding environment including, e.g., one or more Hall sensors, a magnetic gradient sensor, an antenna, an RF sensing device, etc. Some embodiments of IMD 12 may not include sensors 28.

Power source 30 is configured to supply power to one or more of the components within IMD 12. Power source 30 may include a rechargeable or non-rechargeable battery. A non-rechargeable battery may be capable of holding a charge for several years, while a rechargeable battery may be inductively charged from an external device, e.g., on a daily or weekly basis. Examples of a rechargeable battery include, for example, a lithium ion battery, a lithium polymer battery or a supercapacitor. Each of the components within IMD 12 may be electrically coupled to power source 30.

Electrodes 14 include one or more electrodes that are configured to deliver pacing therapy to the heart and/or to sense electrical signals from of the heart. Each of the electrodes may be formed from conductive material. Electrodes 14 may include any combination of lead-based electrodes and leadless electrodes. A lead-based electrode may be a conductor disposed within an elongated insulative lead body, and a leadless electrode may be a conductor that is affixed to the housing of IMD 12 without necessarily including an insulative lead body that extends beyond the housing of IMD 12.

Electrodes 14 may include one or more electrodes implanted within and/or affixed to the surface of one or more cardiac chambers and/or veins. For example, individual electrodes 14 may be implanted within and/or affixed to any combination of a right atrium (RA), a left atrium (LA), a right ventricle (RV), a left ventricle (LV), a coronary sinus, or any other region associated with the heart.

In some examples, two or more electrodes may both be implanted within the same particular region of the heart and together form a pair of electrodes configured to provide pacing therapy to the particular region of the heart and/or to sense electrical activity associated with the particular region of the heart. The pacing therapy provided by pairs of electrodes implanted within a common region of the heart may be referred to herein as bipolar pacing therapy. For lead-based electrodes, each of the pair of electrodes may be included within a single lead implanted within a region of the heart. In such cases, the lead may be referred to by the particular region of the heart into which it is implanted, e.g., an RA lead, an LA lead, an RV lead, an LV lead, etc. In some implementations, a single lead may include a tip electrode and ring electrode configured to provide bipolar pacing therapy and/or sensing of electrical activity. For leadless electrodes, a pair of electrodes may be affixed to a housing of IMD 12 and configured to provide bipolar pacing therapy and/or sensing of electrical activity.

In additional examples, a single electrode may be implanted within a particular region of the heart and provide pacing therapy with respect to an electrode affixed to or formed from the housing of IMD 12. The pacing therapy provided by such a configuration of electrodes may be referred to herein as unipolar pacing therapy. For example, for lead-based electrodes, a lead may be implanted within a region of the heart that includes a single electrode and unipolar pacing therapy may be provided with respect to a "can" electrode disposed on the housing of IMD 12.

In some examples, programmer 16 may be a handheld computing device, computer workstation, or networked computing device. Programmer 16 includes a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 16 can additionally or alternatively include a peripheral pointing device, such as a mouse, via which a user may interact with the user interface. In some examples, a display of programmer 16 may include a touch screen display, and a user may interact with programmer 16 via the display. The user may also interact with programmer 16 or IMD 12 remotely via a networked computing device.

Programmer 16 is configured to receive user input from a user, such as a clinician or patient for example, and to program IMD 12 based on the user input. In some examples, programmer 16 may receive user input that includes a user command instructing IMD 12 to switch the current operational mode of IMD 12 to either a normal mode or an EMI-safe mode. Programmer 16 may receive the user command via the user interface, e.g., by touching one or more keys on a keypad, moving or clicking a mouse, or touching a display. In response to receiving the user command, programmer 16 may transmit, via wireless telemetry for example, the command to IMD 12 instructing IMD 12 to switch the current operational state of IMD 12 into either a normal mode or an EMI-safe mode. In additional examples, programmer 16 may receive user input specifying one or more pacing therapy parameters and/or configuration parameters for IMD 12, and program IMD 12 according to the received parameters.

Programmer 16 may also receive data from IMD 12 and present the data to the user. For example, programmer 16 may receive the current operational mode of IMD 12 and/or the current pacing mode of IMD 12 and present the data to a user of programmer 16. Programmer 16 may also present cardiac data, such as an EGM or other sensed data received from IMD 12 to a user of programmer 16.

Figure 2:
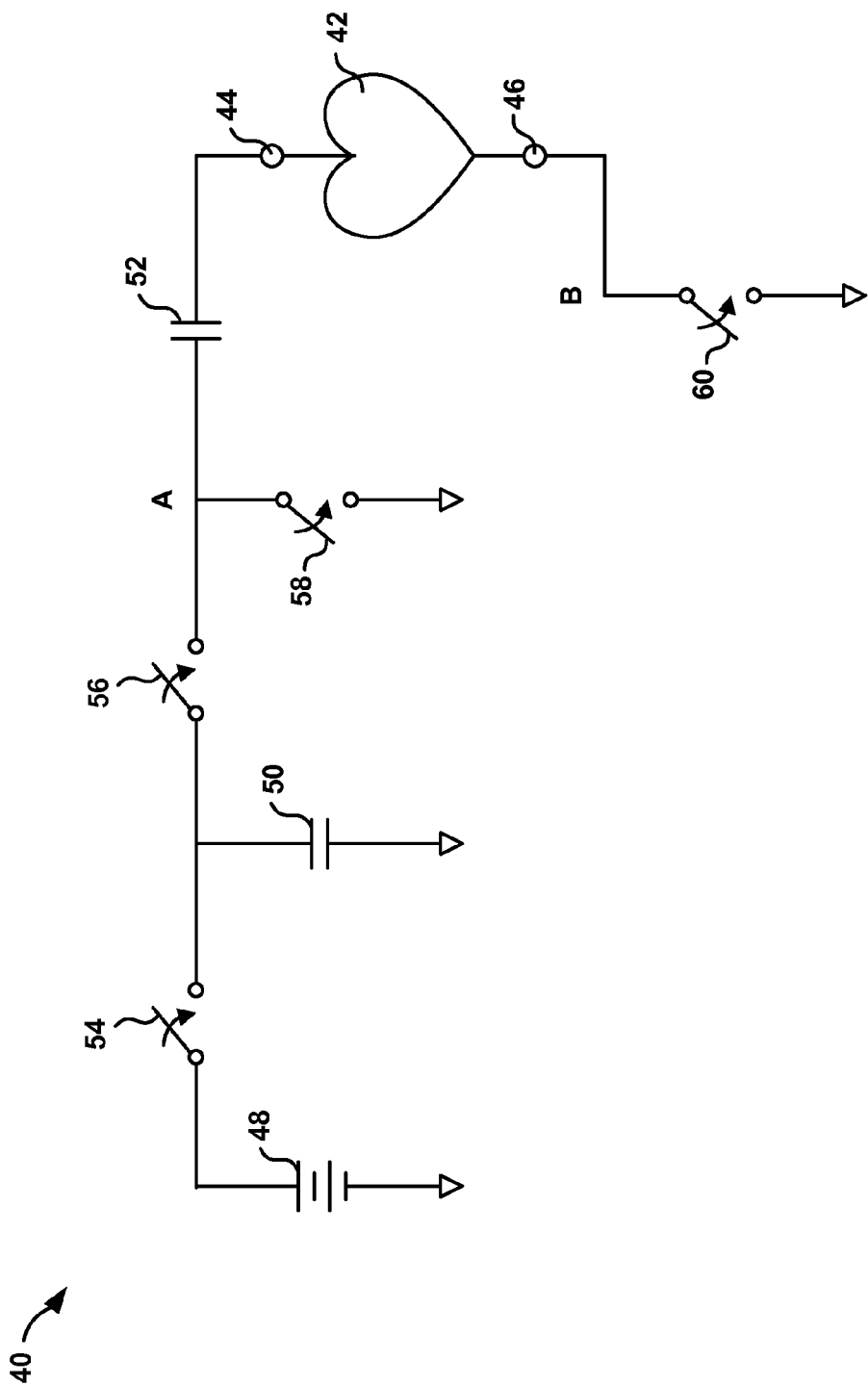
FIG. 2 is a schematic diagram illustrating an example pacing output circuit that may be used to implement the techniques of this disclosure.

FIG. 2 is a schematic diagram illustrating an example pacing output module 40 that may be used to implement the techniques of this disclosure. In some examples, pacing output module 40 may correspond to pacing output module 20 within IMD 12 of FIG. 1. Pacing output module 40 is configured to deliver a pacing pulse to cardiac tissue 42 via electrodes 44, 46. In some cases, electrodes 44, 46 may correspond, respectively, to a tip electrode and a ring electrode of a pacing lead electrically coupled to IMD 12. Pacing output module 40 includes a charge pump 48, a holding capacitor 50, a coupling capacitor 52, and switches 54, 56, 58, 60.

Charge pump 48 is configured to charge holding capacitor 50 when switch 54 is closed. Holding capacitor 50 is configured to hold a charge that will used to deliver a pacing pulse to cardiac tissue 42. Coupling capacitor 52 is configured to block DC currents from traveling through cardiac tissue 42 during the delivery of a pacing pulse. Switches 54, 56, 58, 60 are each configured to receive a respective control signal from a control unit, e.g., pacing timing and control module 36 in FIG. 1, and to open or close in response to the control signal.

Charge pump 48 includes a first terminal electrically coupled to a first terminal of switch 54 and a second terminal electrically coupled to a common voltage. Holding capacitor 50 includes a first terminal electrically coupled to the second terminal of switch 54 and to a first terminal switch 56. Holding capacitor 50 also includes a second terminal electrically coupled to the common voltage. Coupling capacitor 52 includes a first terminal electrically coupled to a second terminal of switch 56 and to a first terminal switch 58. Switch 58 includes a second terminal electrically coupled to the common voltage. Coupling capacitor 52 includes a second terminal electrically coupled to electrode 44. Switch 60 includes a first terminal electrically coupled to electrode 46 and a second terminal electrically coupled to the common voltage.

Prior to the delivery of a pacing pulse, pacing output module 40 may be switched into a charging configuration. In the charging configuration, switch 54 is closed, switch 56 is open, and switches 58, 60 may be either open or closed. While operating in the charging configuration, charge pump 48 charges up holding capacitor 50.

To deliver the pacing pulse, pacing output module 40 switches into a pacing configuration. In the pacing configuration, switch 54 is open to isolate charge pump 48 from a direct path to cardiac tissue 42, switch 56 is closed, switch 58 is open, and switch 60 is closed. While operating in the pacing configuration, holding capacitor 50 is discharged through an electrical pathway that includes closed switch 56, coupling capacitor 52, electrode 44, cardiac tissue 42, electrode 46 and closed switch 60.

Pacing output module 40 may also be placed into a passive recharge configuration. In such a configuration, switch 56 is open, switch 58 is closed, switch 60 is closed and switch 54 may be either open or closed. The passive recharge configuration effectively couples both terminals of coupling capacitor 52 to a common voltage in order to discharge coupling capacitor 52. For example, a first terminal is electrically coupled to the common voltage via switch 58 and the second terminal is electrically coupled to the common voltage through electrode 44, cardiac tissue 42, electrode 46 and switch 60. The configuration may be referred to as a passive recharge configuration because the capacitor is discharged without actively driving a current through the circuit path.

In some examples, pacing output module 40 may be placed into the passive recharge configuration in order to perform a post-stimulation passive recharge cycle. The delivery of the pacing pulse may cause a residual charge to build-up on coupling capacitor 52. This charge may be referred to as a polarization voltage or after-potential. The post-stimulus charge build-up on coupling capacitor 52 may interfere with the sensing of electrical signals via electrodes 44, 46 and/or interfere with the delivery of subsequent pacing pulses. By performing a post-stimulation passive recharge cycle, the charge build-up on coupling capacitor 52 caused by the delivery of previous pacing pulse may be reduced and/or eliminated. The post-stimulation passive recharge cycle, however, does not compensate for any charging of coupling capacitor 52 that may occur after the completion of the post-stimulation passive recharge cycle and prior to the delivery of the subsequent pacing pulse. Charging of coupling capacitor 52 during such a time frame may occur when the IMD is subject to EMI. If capacitor 52 is not discharged prior to delivery of the next pacing pulse, the EMI-induced charge build-up may cause the magnitude of the next pacing pulse to be shifted, which may cause overstimulation, understimulation or affect the capture threshold, i.e., the amount of voltage that needs to be produced by a pulse generator to cause a depolarization of the heart.

In order to compensate for EMI-induced charge on coupling capacitor 52, pacing output circuit 40 may be configured to perform a pre-stimulation passive recharge cycle when the pre-stimulation passive recharge pacing mode is enabled. The pre-stimulation passive recharge cycle may occur during a time frame that is closer to the delivery of the next pacing pulse that the time frame used to perform the post-stimulation passive recharge cycle. For example, the pre-stimulation passive recharge cycle may, in some examples, occur immediately prior to the delivery of a subsequent pacing pulse. By performing a passive recharge cycle in this manner, pacing output module 40 may be able to reduce any charge build-up that occurs between paces due to EMI.

In the example pacing output module 40 of FIG. 2, in order to perform the pre-stimulation passive recharge cycle, pacing output module 40 is placed into the same passive recharge configuration as that which is used to perform the post-stimulation passive recharge cycle. However, in other examples, different passive recharge configurations may be used to discharge coupling capacitor 52.

Figure 3:
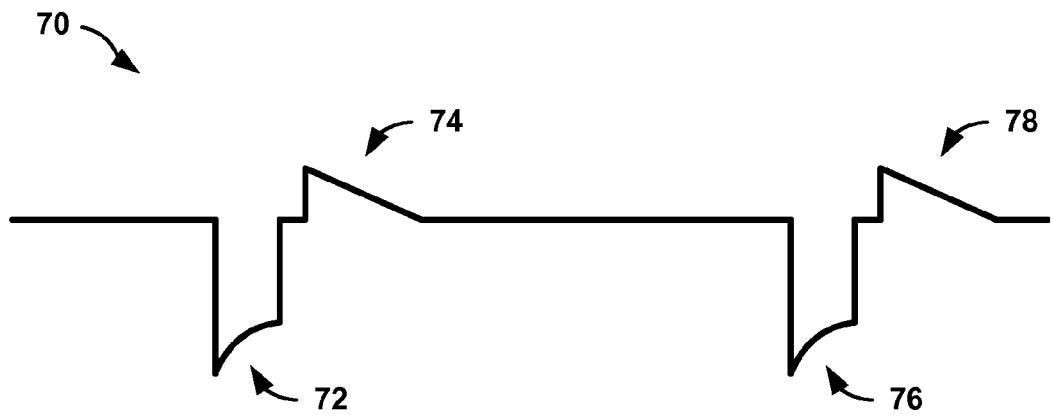
FIG. 3 is a conceptual diagram illustrating an example pacing waveform for a normal pacing mode according to this disclosure.

FIG. 3 is a conceptual diagram illustrating an example pacing waveform 70 for a normal pacing mode according to this disclosure. Pacing waveform 70 may represent the electrical voltage between nodes A and B illustrated in pacing output module 40 of FIG. 2. As shown in FIG. 3, IMD 12 delivers a pacing pulse 72. Following the delivery of pacing pulse 72, IMD 12 performs a post-stimulation passive recharge cycle 74. After a delay period, IMD 12 delivers a subsequent pacing pulse 76. Following the delivery of subsequent pacing pulse 76, IMD 12 performs a post-stimulation passive recharge cycle 78. As is shown in FIG. 3, when pacing according to the normal pacing mode, a pre-stimulation passive recharge cycle does not occur between the completion of post-stimulation passive recharge cycle 74 and the delivery of pacing pulse 76.

Figure 4:
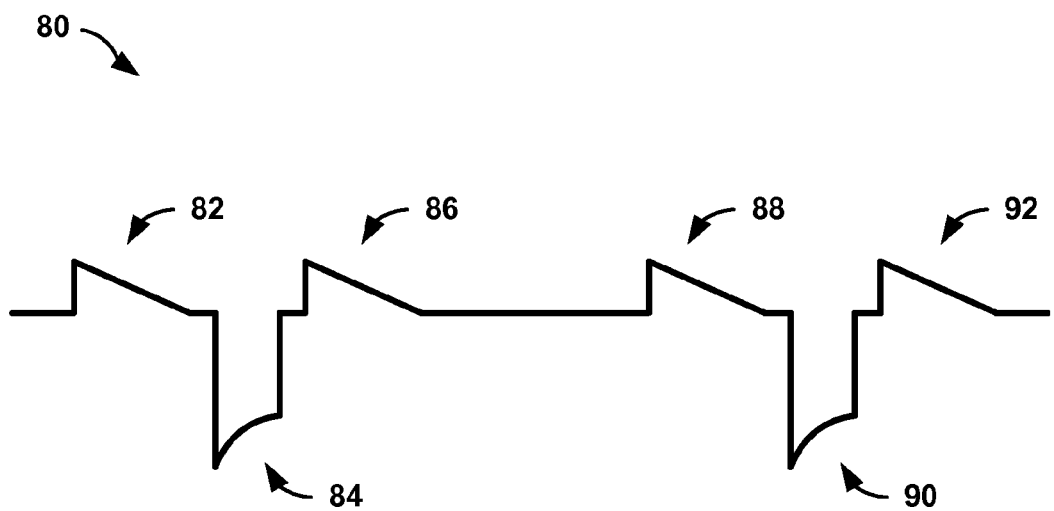
FIG. 4 is a conceptual diagram illustrating an example pacing waveform for a pre-stimulation passive recharge pacing mode according to this disclosure.

FIG. 4 is a conceptual diagram illustrating an example pacing waveform 80 for a pre-stimulation passive recharge pacing mode according to this disclosure. Pacing waveform 80 may represent the electrical voltage between nodes A and B illustrated in pacing output module 40 of FIG. 2. As shown in FIG. 4, IMD 12 performs a pre-stimulation passive recharge cycle 82 prior to the delivery of pacing pulse 84. After the performance of pre-stimulation passive recharge cycle 82, IMD 12 delivers pacing pulse 84. After the delivery of pacing pulse 84, IMD 12 performs a post-stimulation passive recharge cycle 86. After a delay period, IMD 12 performs a pre-stimulation passive recharge cycle 88 prior to the delivery of a subsequent pacing pulse 90. After the performance of pre-stimulation passive recharge cycle 88, IMD 12 delivers subsequent pacing pulse 90. After the delivery of subsequent pacing pulse 90, IMD 12 performs a post-stimulation passive recharge cycle 92. As is shown in FIG. 4, when pacing according to the pre-stimulation passive recharge cycle pacing mode, a pre-stimulation passive recharge cycle 88 occurs between the completion of post-stimulation passive recharge cycle 86 and the delivery of pacing pulse 90.

FIGS. 3 and 4 illustrate example pacing waveforms that have negative polarity pacing pulses and positive polarity residual charges that are discharged during the passive recharge cycles. It should be noted, however, that in other examples, the pacing pulses may be positive polarity pulses and the residual charges may be negative polarity. In additional examples, the residual charge buildup that occurs prior to the delivery of a pacing pulse may be the same as or different than the polarity of the pacing pulse. In further examples, the residual charge buildup that occurs prior to the delivery of a pacing pulse may be the same as or different than the polarity of the charge buildup that occurs after the delivery of a pacing pulse. Although the residual charge build-up that occurs prior to the delivery of a pacing pulse is illustrated as an abrupt transition, in other examples, the residual charge may build-up in a more progressive or continuous manner during the waiting period between the post-stimulation passive recharge cycle and the pre-stimulation passive recharge cycle.

Figure 5:
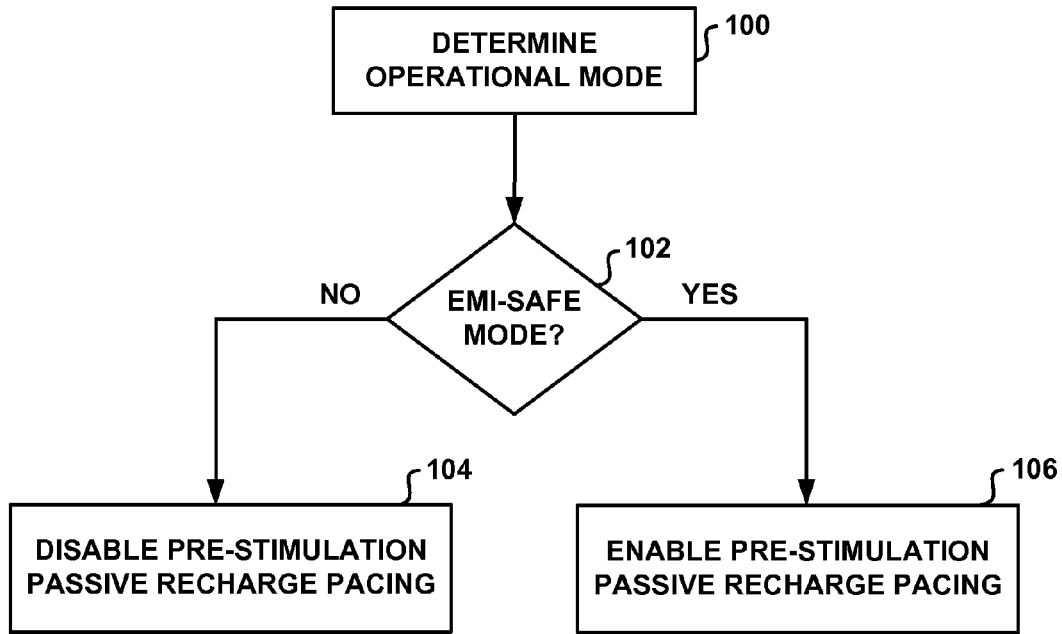
FIG. 5 is a flow diagram illustrating an example technique for selectively enabling and disabling a pre-stimulation passive recharge pacing mode according to this disclosure.

FIG. 5 is a flow diagram illustrating an example technique for selectively enabling and disabling a pre-stimulation passive recharge pacing mode according to this disclosure. Pacing mode selection module 34 determines the current operational mode of IMD 12 (100). For example, pacing mode selection module 34 may receive the current operational mode from EMI-safe mode switching module 32 and/or access memory 24 to retrieve the current operational mode. Pacing mode selection module 34 determines whether IMD 12 is operating in an EMI-safe mode (102). If IMD 12 is not operating in the EMI-safe mode, pacing mode selection module 34 disables the pre-stimulation passive recharge pacing mode (104). If IMD 12 is operating in the EMI-safe mode, pacing mode selection module 34 enables the pre-stimulation passive recharge pacing mode (106). In some examples, the EMI-safe mode may be an MRI-safe mode.

Figure 6:
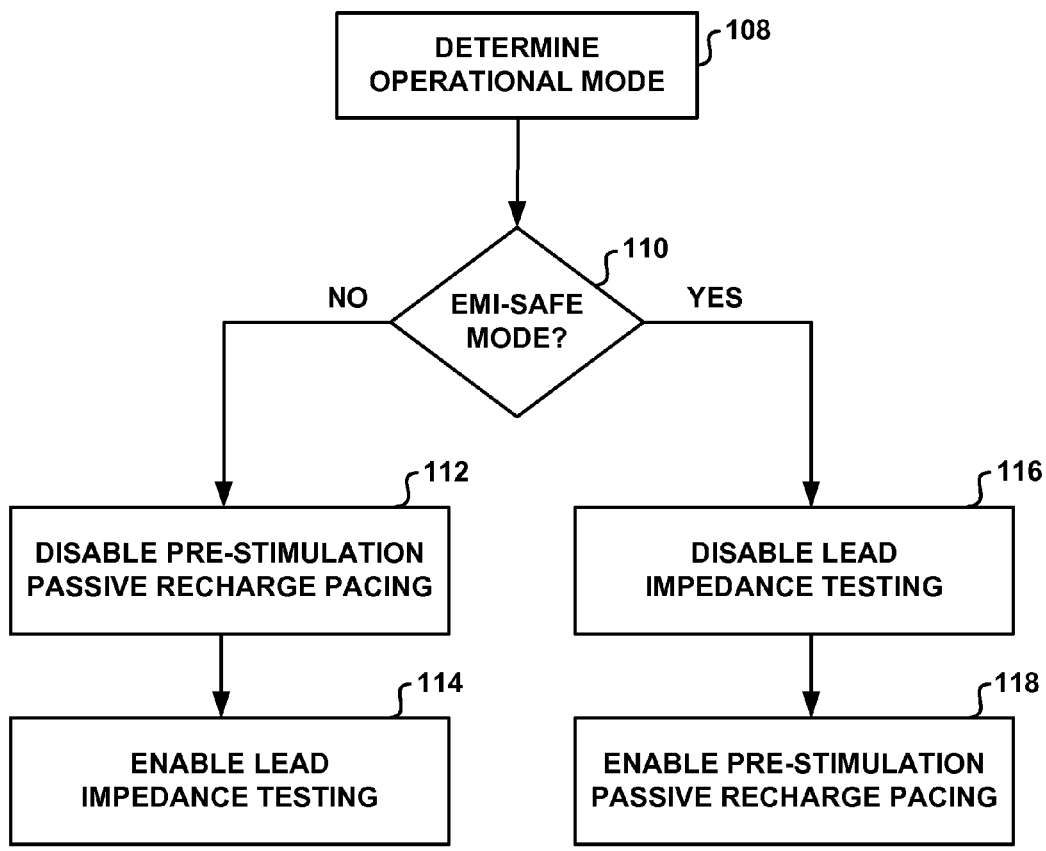
FIG. 6 is a flow diagram illustrating another example technique for selectively enabling and disabling a pre-stimulation passive recharge pacing mode according to this disclosure.

FIG. 6 is a flow diagram illustrating another example technique for selectively enabling and disabling a pre-stimulation passive recharge pacing mode according to this disclosure. Pacing mode selection module 34 determines the current operational mode of IMD 12 (108). For example, pacing mode selection module 34 may receive the current operational mode from EMI-safe mode switching module 32 and/or access memory 24 to retrieve the current operational mode. Pacing mode selection module 34 determines whether IMD 12 is operating in an EMI-safe mode (110). If IMD 12 is not operating in the EMI-safe mode, pacing mode selection module 34 disables the pre-stimulation passive recharge pacing mode (112), and enables lead impedance testing (114). If IMD 12 is operating in the EMI-safe mode, pacing mode selection module 34 disables lead impedance testing (116) and enables the pre-stimulation passive recharge pacing mode (118). In some examples, the EMI-safe mode may be an MRI-safe mode and/or a magnet mode.

Figure 7:
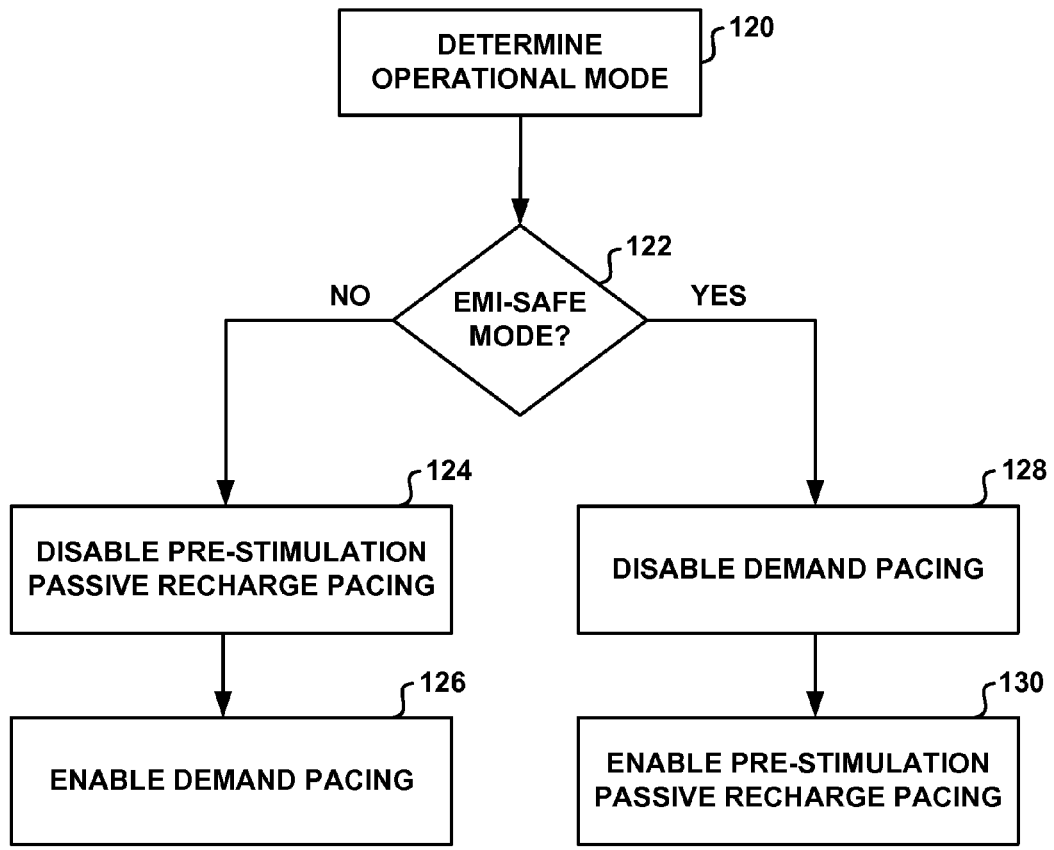
FIG. 7 is a flow diagram illustrating another example technique for selectively enabling and disabling a pre-stimulation passive recharge pacing mode according to this disclosure.

FIG. 7 is a flow diagram illustrating another example technique for selectively enabling and disabling a pre-stimulation passive recharge pacing mode according to this disclosure. Pacing mode selection module 34 determines the current operational mode of IMD 12 (120). For example, pacing mode selection module 34 may receive the current operational mode from EMI-safe mode switching module 32 and/or access memory 24 to retrieve the current operational mode.

Pacing mode selection module 34 determines whether IMD 12 is operating in an EMI-safe mode (122). If IMD 12 is not operating in the EMI-safe mode, pacing mode selection module 34 disables the pre-stimulation passive recharge pacing mode (124), and enables a demand pacing mode (126). Enabling the demand pacing mode may also correspond to disabling an asynchronous pacing mode. If IMD 12 is operating in the EMI-safe mode, pacing mode selection module 34 disables the demand pacing mode (128) and enables the pre-stimulation passive recharge pacing mode (130). Disabling the demand pacing mode may also correspond to enabling the asynchronous pacing mode. In some examples, the EMI-safe mode may be an MRI-safe mode and/or a magnet mode.

Figure 8:
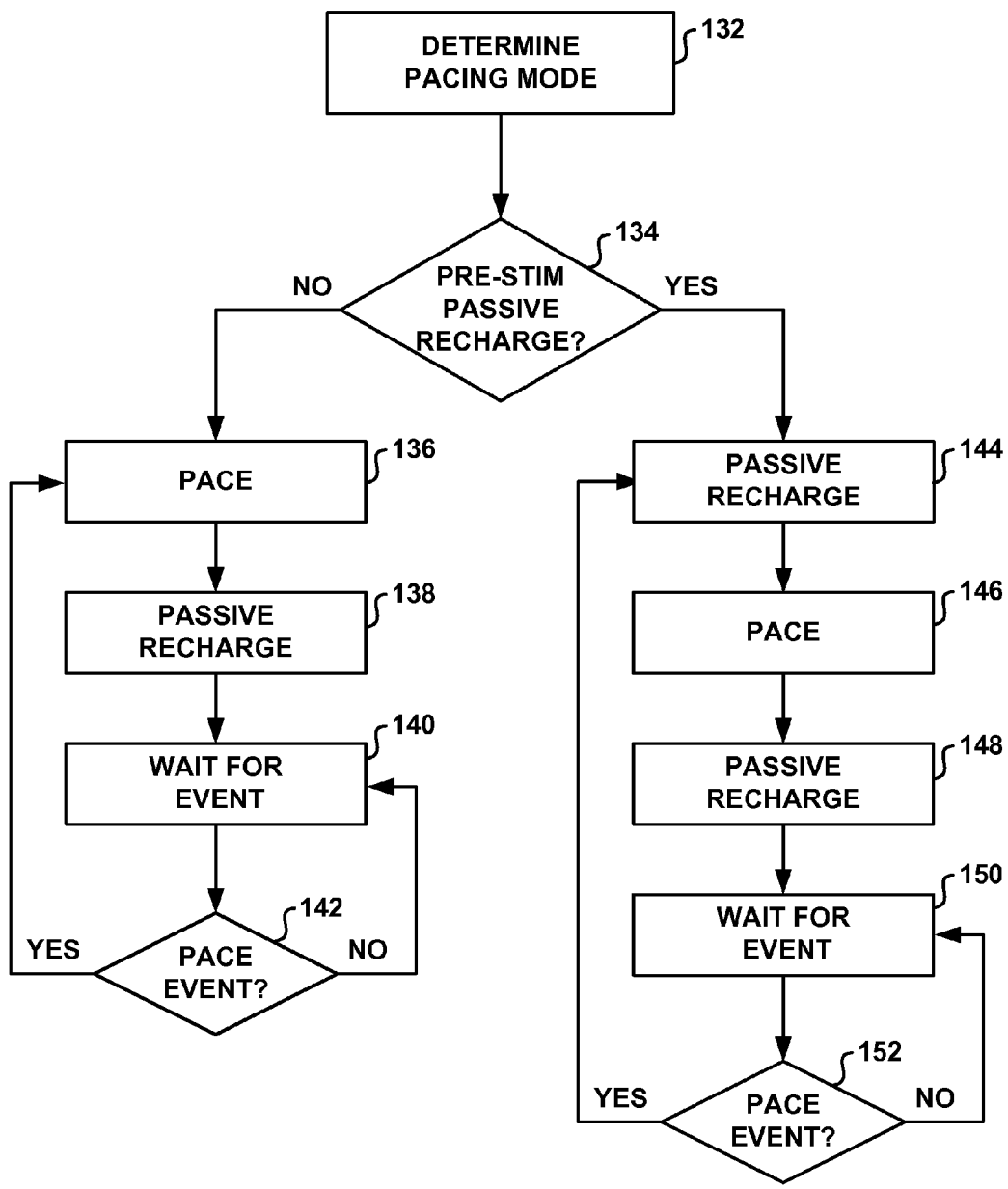
FIG. 8 is a flow diagram illustrating an example technique for selectively delivering pacing therapy according to a normal pacing mode and a pre-stimulation passive recharge pacing mode according to this disclosure.

FIG. 8 is a flow diagram illustrating an example technique for selectively delivering pacing therapy according to a normal pacing mode and a pre-stimulation passive recharge pacing mode according to this disclosure. Pacing timing and control module 36 determines the current pacing mode of IMD 12 (132). For example, pacing timing and control module 36 may receive the current pacing mode from pacing mode selection module 34 and/or access memory 24 to retrieve the current pacing mode. Pacing timing and control module 36 determines whether the current pacing mode is the pre-stimulation passive recharge pacing mode or the normal pacing mode (134).

If the current pacing mode is not the pre-stimulation passive recharge pacing mode (i.e. the current pacing mode is the normal pacing mode), IMD 12 delivers a pacing pulse (136). For example, pacing timing and control module 36 may switch pacing output module 20 into a pacing configuration. After delivering the pacing pulse, IMD 12 performs a post-stimulation passive recharge cycle (138). For example, pacing timing and control module 36 may switch pacing output module 20 into a passive recharge configuration. After delivering the pacing pulse, IMD 12 waits for a pacing event (140). The pacing event may be any event that triggers the delivery of a subsequent pacing pulse. For example, pacing timing and control module 36 may wait for one or more timers to expire and/or wait for a sensed event to occur in order to trigger the delivery of a subsequent pacing pulse. IMD 12 determines if a pacing event has occurred (142). If a pacing event has not yet occurred, IMD 12 returns to process box 140 and continues to wait for a pacing event. If a pacing event has occurred, IMD 12 returns to process box 136 and delivers a subsequent pacing pulse.

If the current pacing mode is the pre-stimulation passive recharge pacing mode, IMD 12 performs a pre-stimulation passive recharge cycle prior to delivery a pacing pulse (144). For example, pacing timing and control module 36 may switch pacing output module 20 into a passive recharge configuration. After performing the passive recharge cycle, IMD 12 proceeds to deliver a pacing pulse (146). For example, pacing timing and control module 36 may switch pacing output module 20 into a pacing configuration. After delivering the pacing pulse, IMD 12 performs a post-stimulation passive recharge cycle (148). For example, pacing timing and control module 36 may switch pacing output module 20 into the passive recharge configuration. After delivering the pacing pulse, IMD 12 waits for a pacing event (150). The pacing event may be any event that triggers the delivery of a subsequent pacing pulse. For example, pacing timing and control module 36 may wait for one or more timers to expire and/or wait for a sensed event to occur in order to trigger the delivery of a subsequent pacing pulse. IMD 12 determines if a pacing event has occurred (152). If a pacing event has not yet occurred, IMD 12 returns to process box 150 and continues to wait for a pacing event. If a pacing event has occurred, IMD 12 returns to process box 144 and performs a pre-stimulation passive recharge cycle.

As shown in FIG. 8, when pacing according to the pre-stimulation passive recharge mode, IMD 12 may deliver a pacing pulse (146), perform a first passive recharge cycle after delivering of the pacing pulse (148), and perform a second passive recharge cycle after the first passive recharge cycle and prior to delivery of a subsequent pacing pulse (144).

As also shown in FIG. 8, when pacing according to the pre-stimulation passive recharge mode, IMD 12 may perform a passive recharge cycle (144), and unconditionally deliver a pacing pulse as a next sequential step after performing the passive recharge cycle (146). By unconditionally delivering the pacing pulse as a next sequential step, it is meant that IMD 12 does not need to wait for a subsequent pacing event to occur in order to deliver the pacing pulse. In contrast, after performing the passive recharge cycle in process box 148, IMD 12 waits until a pacing event occurs (152) prior to delivering a subsequent pacing pulse. In other words, the delivery of a pacing pulse after the passive recharge cycle in process box 148 is conditioned on the occurrence of a pace event.

As is also shown in FIG. 8, wherein delivering the pacing therapy according to the normal pacing mode, IMD 12 may deliver a first pacing pulse (136). After delivering the first pacing pulse, IMD 12 may unconditionally perform a passive recharge cycle as a next sequential step after delivering the first pacing pulse (138). By unconditionally performing the passive recharge cycle as a next sequential step, it is meant that IMD 12 does not need to wait for a subsequent pacing event to occur after delivering the pacing pulse. IMD 12 delivers a second pacing pulse (136) after performing the passive recharge cycle without performing any intervening passive recharge cycles in between the passive recharge cycle and the second pacing pulse. In other words, between process box 138 and process box 136 of a subsequent pacing cycle, no passive recharge cycle occurs. In contrast, when pacing according to the pre-stimulation passive recharge mode, a passive recharge cycle occurs between process box 148 and process box 146 of a subsequent pacing cycle.

Figure 9:
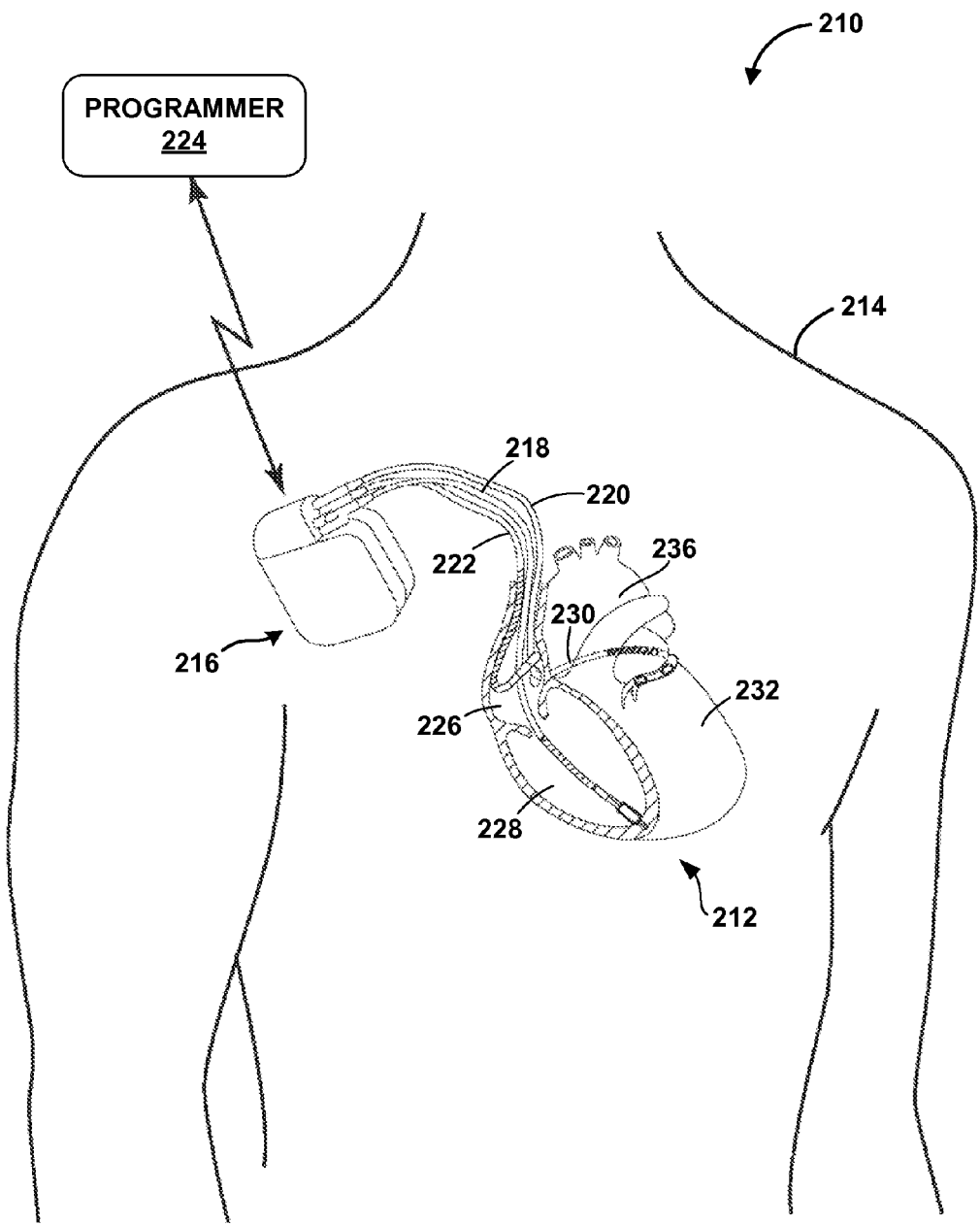
FIG. 9 is a conceptual diagram illustrating an example implementation of the therapy system of FIG. 1 according to this disclosure.

FIG. 9 is a conceptual diagram illustrating an example therapy system 210 that may be used to implement IMD 12 of FIG. 1 according to this disclosure. Therapy system 210 is configured to provide therapy to heart 212 of patient 214. Patient 214 is ordinarily, but not necessarily, a human patient. Therapy system 210 includes IMD 216, leads 218, 220, 222, and programmer 224. IMD 216 is coupled to each of leads 218, 220, 222.

IMD 216 may be, for example, a device that provides cardiac rhythm management therapy to heart 212, and may include, for example, an implantable pacemaker, cardioverter, and/or defibrillator that provides therapy to heart 212 of patient 214 via electrodes coupled to one or more of leads 218, 220, and 222. In some examples, IMD 216 may deliver pacing pulses, but not cardioversion or defibrillation shocks, while in other examples, IMD 216 may deliver cardioversion and/or defibrillation shocks in addition to pacing pulses. In additional examples, IMD 216 may provide cardiac resynchronization therapy in addition to or in lieu of pacing pulses, cardioversion shocks, and/or defibrillation shocks.

Leads 218, 220, 222 extend into the heart 212 of patient 214 to sense electrical activity of heart 212 and/or deliver electrical stimulation to heart 212. In the example shown in FIG. 9, right ventricular (RV) lead 218 extends through one or more veins (not shown), the superior vena cava (not shown), and right atrium 226, and into right ventricle 228. Left ventricular (LV) coronary sinus lead 220 extends through one or more veins, the vena cava, right atrium 226, and into the coronary sinus 230 to a region adjacent to the free wall of left ventricle 232 of heart 212. Right atrial (RA) lead 222 extends through one or more veins and the vena cava, and into right atrium 226 of heart 212. In other examples, therapy system 210 may include an additional lead or lead segment (not shown in FIG. 9) that deploys one or more electrodes within the vena cava or other vein. These electrodes may allow alternative electrical sensing configurations that may provide improved sensing accuracy in some patients.

IMD 216 senses electrical signals attendant to the depolarization and repolarization of heart 212 via electrodes coupled to at least one of the leads 218, 220, 222. In some examples, IMD 216 provides pacing pulses to heart 212 based on the electrical signals sensed within heart 212. These electrical signals sensed within heart 212 may also be referred to as cardiac signals or electrical cardiac signals. The configurations of electrodes used by IMD 216 for sensing and pacing may be unipolar or bipolar. IMD 216 may also provide defibrillation therapy and/or cardioversion therapy via electrodes located on at least one of the leads 218, 220, 222. IMD 216 may detect arrhythmia of heart 212, such as fibrillation of ventricles 228 and 232, and deliver cardioversion or defibrillation therapy to heart 212 in the form of electrical pulses. In some examples, IMD 216 may be programmed to deliver a progression of therapies, e.g., pulses with increasing energy levels, until a tachyarrhythmia of heart 212 is stopped. IMD 216 detects tachycardia or fibrillation employing one or more tachycardia or fibrillation detection techniques known in the art.

In some examples, programmer 224 may be a handheld computing device, computer workstation, or networked computing device. Programmer 224 includes a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 224 can additionally or alternatively include a peripheral pointing device, such as a mouse, via which a user may interact with the user interface. In some examples, a display of programmer 224 may include a touch screen display, and a user may interact with programmer 224 via the display. It should be noted that the user may also interact with programmer 224 or IMD 216 remotely via a networked computing device.

A user, such as a physician, technician, surgeon, electrophysiologist, or other clinician, may interact with programmer 224 to communicate with IMD 216. For example, the user may interact with programmer 224 to retrieve physiological or diagnostic information from IMD 216. A user may also interact with programmer 224 to program IMD 216, e.g., select values for operational parameters of IMD 216.

For example, the user may use programmer 224 to retrieve information from IMD 216 regarding the rhythm of heart 212, trends therein over time, or tachyarrhythmia episodes. As another example, the user may use programmer 224 to retrieve information from IMD 216 regarding other sensed physiological parameters of patient 214, such as electrical depolarization/repolarization signals from the heart (referred to as "electrogram" or EGM), intracardiac or intravascular pressure, activity, posture, respiration, heart rate, heart sounds, or thoracic impedance. As another example, the user may use programmer 224 to retrieve information from IMD 216 regarding the performance or integrity of IMD 216 or other components of system 210, such as leads 218, 220 and 222, or a power source of IMD 216.

The user may use programmer 224 to program a therapy progression, select electrodes used to deliver defibrillation shocks, select waveforms for the defibrillation shocks, or select or configure a fibrillation detection algorithm for IMD 216. The user may also use programmer 224 to program similar aspects of other therapies provided by IMD 216, such as cardioversion or pacing therapies. In some examples, the user may activate certain features of IMD 216 by entering a single command via programmer 224, such as depression of a single key or combination of keys of a keypad or a single point-and-select action with a pointing device.

According to this disclosure IMD 216 includes a pacing mode selector that is configured to selectively enable and disable a pre-stimulation passive recharge pacing mode for IMD 216 based on whether the IMD 216 is operating in an EMI-safe mode. For example, the pacing mode selector may enable the pre-stimulation passive recharge pacing mode when the IMD is operating in the EMI-safe mode, and disable the pre-stimulation passive recharge pacing mode when the IMD is not operating in the EMI-safe mode.

Figure 10:
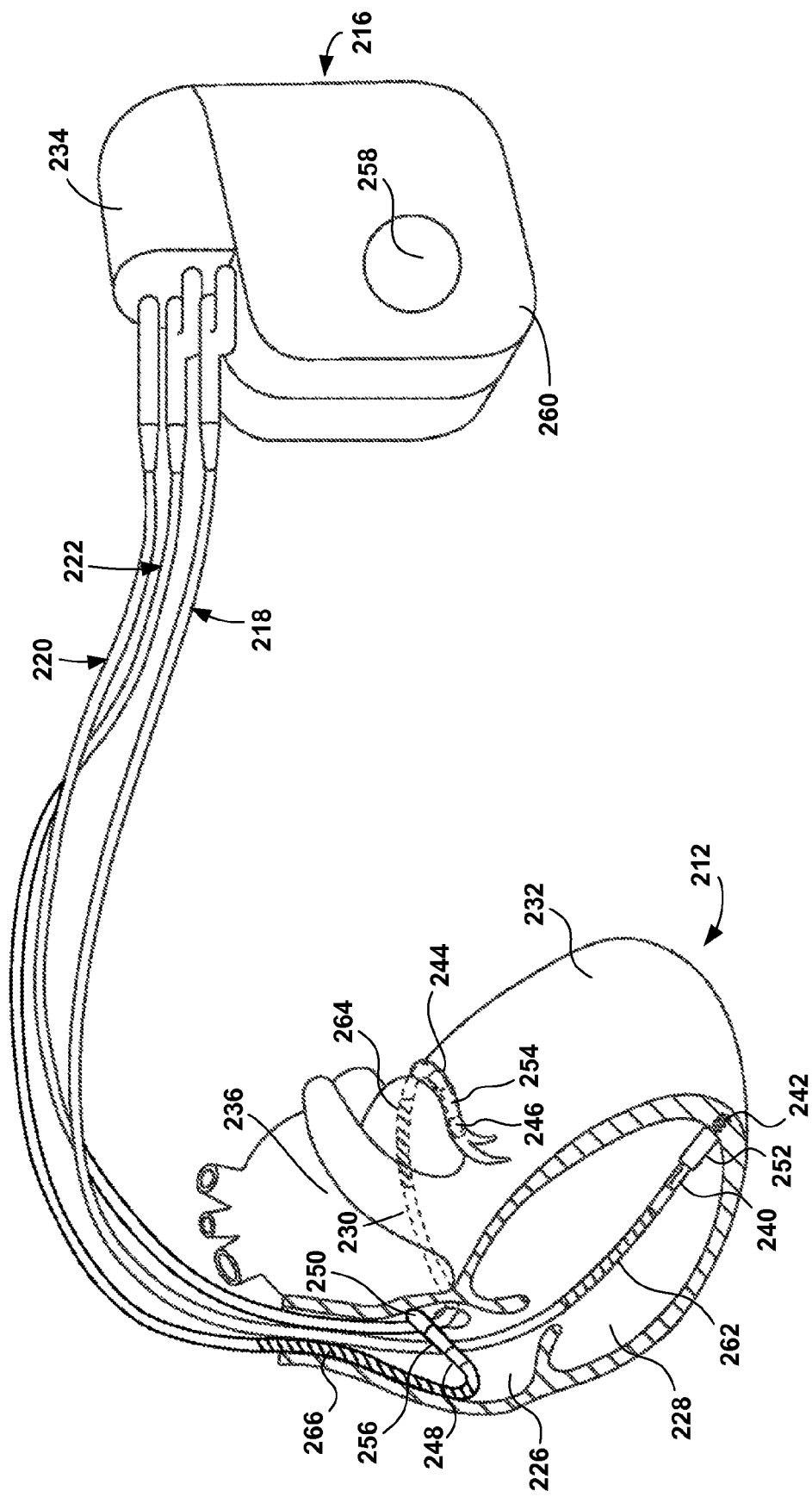
FIG. 10 is a conceptual diagram illustrating the IMD and leads of the example therapy system of FIG. 9 in greater detail.

FIG. 10 is a conceptual diagram illustrating IMD 216 and leads 218, 220 and 222 of therapy system 210 in greater detail. As shown in FIG. 10, IMD 216 includes a housing 260 and a connector block 234. Leads 218, 220, 222 may be electrically coupled to a signal generator and a sensing module of IMD 216 via connector block 234. In some examples, proximal ends of leads 218, 220, 222 may include electrical contacts that electrically couple to respective electrical contacts within connector block 234 of IMD 216. In addition, in some examples, leads 218, 220, 222 may be mechanically coupled to connector block 234 with the aid of set screws, connection pins, snap connectors, or another suitable mechanical coupling mechanism.

Each of the leads 218, 220, 222 includes an elongated insulative lead body, which may carry a number of concentric coiled conductors separated from one another by tubular insulative sheaths. Other lead configurations are also contemplated, such as configurations that do not include coiled conductors. In the illustrated example, bipolar electrodes 240 and 242 are located proximate to a distal end of lead 218 in RV 228. In addition, bipolar electrodes 244 and 246 are located proximate to a distal end of lead 220 in LV 232 and bipolar electrodes 248 and 250 are located proximate to a distal end of lead 222 in RA 226. Although no electrodes are located in LA 236 in the illustrated example, other examples may include electrodes in LA 236.

Electrodes 240, 244, and 248 may take the form of ring electrodes, and electrodes 242, 246, and 250 may take the form of extendable helix tip electrodes mounted retractably within insulative electrode heads 252, 254, and 256, respectively. In other examples, one or more of electrodes 242, 246, and 250 may take the form of small circular electrodes at the tip of a tined lead or other fixation element. Leads 218, 220, 222 also include elongated electrodes 262, 264, 266, respectively, which may take the form of a coil. Each of the electrodes 240, 242, 244, 246, 248, 250, 262, 264, and 266 may be electrically coupled to a respective one of the conductors within the lead body of its associated lead 218, 220, 222, and thereby coupled to respective ones of the electrical contacts on the proximal end of leads 218, 220, 222.

In some examples, as illustrated in FIG. 10, IMD 216 includes one or more housing electrodes, such as housing electrode 258, which may be formed integrally with an outer surface of hermetically-sealed housing 260 of IMD 216 or otherwise coupled to housing 260. Housing electrode 258 may be defined, in some examples, by an uninsulated portion of an outward facing portion of housing 260 of IMD 216. Other divisions between insulated and uninsulated portions of housing 260 may be employed to define two or more housing electrodes. In some examples, housing electrode 258 comprises substantially all of housing 260. As described in further detail with reference to FIG. 13, housing 260 may enclose a signal generator that generates therapeutic stimulation, such as cardiac pacing pulses and defibrillation shocks, as well as a sensing module for monitoring the rhythm of heart 212.

IMD 216 may sense electrical signals attendant to the depolarization and repolarization of heart 212 via electrodes 240, 242, 244, 246, 248, 250, 258, 262, 264, and 266. The electrical signals are conducted to IMD 216 from the electrodes via the respective leads 218, 220, 222 or, in the case of housing electrode 258, a conductor couple to housing electrode 258. IMD 216 may sense such electrical signals via any bipolar combination of electrodes 240, 242, 244, 246, 248, 250, 258, 262, 264, and 266. Furthermore, any of the electrodes 240, 242, 244, 246, 248, 250, 258, 262, 264, and 266 may be used for unipolar sensing in combination with housing electrode 258.

Any multipolar combination of two or more of electrodes 240, 242, 244, 246, 248, 250, 258, 262, 264, and 266 may be considered a sensing electrode configuration. Usually, but not necessarily, a sensing electrode configuration is a bipolar electrode combination on the same lead, such as electrodes 240 and 242 of lead 218. On one lead having three electrodes, there may be at least three different sensing electrode configurations available to IMD 216. These sensing electrode configurations are, for the example of lead 218, tip electrode 242 and ring electrode 240, tip electrode 242 and elongated electrode 262, and ring electrode 240 and elongated electrode 262. However, some examples may utilize sensing electrode configurations having electrodes of two different leads. Further, a sensing electrode configuration may utilize housing electrode 258, which may provide a unipolar sensing electrode configuration. In some examples, a sensing electrode configuration may comprise multiple housing electrodes 258. In any sensing electrode configuration, the polarity of each electrode in the may be configured as appropriate for the application of the sensing electrode configuration.

In some examples, IMD 216 delivers pacing pulses via bipolar combinations of electrodes 240, 242, 244, 246, 248 and 250 to produce depolarization of cardiac tissue of heart 212. In additional examples, IMD 216 delivers pacing pulses via any of electrodes 240, 242, 244, 246, 248 and 250 in combination with housing electrode 258 in a unipolar configuration. Furthermore, IMD 216 may deliver cardioversion or defibrillation shocks to heart 212 via any combination of elongated electrodes 262, 264, 266, and housing electrode 258. Electrodes 258, 262, 264, 266 may also be used to deliver cardioversion shocks to heart 212. Electrodes 262, 264, 266 may be fabricated from any suitable electrically conductive material, such as, but not limited to, platinum, platinum alloy, Titanium nitride or other materials known to be usable in implantable defibrillation electrodes.

The configuration of therapy system 210 illustrated in FIGS. 9 and 10 is merely one example of a therapy system in which the techniques in this disclosure may be applied. In other examples, a therapy system may include epicardial leads and/or patch electrodes instead of or in addition to the implanted leads 218, 220, 222 illustrated in FIG. 9. Further, housing 260 of IMD 216 need not be implanted within patient 214. In examples in which housing 260 is not implanted in patient 214, IMD 216 may deliver defibrillation pulses and other therapies to heart 212 via percutaneous leads that extend through the skin of patient 214 to a variety of positions within or outside of heart 212.

In other examples of therapy systems that provide electrical stimulation therapy to heart 212, a therapy system may include any suitable number of leads coupled to IMD 216, and each of the leads may extend to any location within or proximate to heart 212. For example, a therapy system may include a single chamber or dual chamber device rather than a three-chamber device as shown in FIG. 9. In a single chamber configuration, IMD 216 is electrically connected to a single lead 220 that includes stimulation and sense electrodes within LV 232. In one example of a dual chamber configuration, IMD 216 is electrically connected to a single lead that includes stimulation and sense electrodes within LV 232 as well as sense and/or stimulation electrodes within RA 226. In another example of a dual chamber configuration, IMD 216 is connected to two leads that extend into a respective one of the RA 228 and LV 232. Other lead configurations are contemplated, and the techniques in this disclosure are not limited to any particular number of leads or configuration of leads.

The techniques of this disclosure may be implemented by an IMD that is configured to provide pacing therapy, and/or cardio-version shocks. In addition, the techniques in this disclosure may also be applied to other types of IMDs. For example, the techniques in this disclosure may be applied to neurostimulators, including deep brain stimulators, spinal cord stimulators, peripheral nerve stimulators, pelvic floor stimulators, gastro-intestinal stimulators, or the like.

The techniques described in this disclosure, including those attributed to control module 18, programmer 16, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), static RAM (SRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
operating an implantable medical device (IMD) in an electromagnetic interference (EMI)-safe mode;
while operating the IMD in the EMI-safe mode:
enabling, with a control module within the IMD, a pre-stimulation passive recharge pacing mode for the IMD;
while operating in the pre-stimulation passive recharge pacing mode, prior to delivery of a pacing pulse via one or more electrodes along a pacing circuit path, discharging a coupling capacitor in the pacing circuit path at a time that is closer to delivery of the pacing pulse than a time of delivery of a previous pacing pulse via the one or more electrodes along the same pacing circuit path; and
while operating in the pre-stimulation passive recharge pacing mode, delivering the pacing pulse via the one or more electrodes along the same pacing circuit path after discharging the coupling capacitor.

2. The method of claim 1, further comprising:
while not operating in the EMI-safe mode, disabling the pre-stimulation passive recharge pacing mode.

3. The method of claim 2, further comprising:
enabling lead impedance testing while the IMD is not operating in the EMI-safe mode; and
disabling lead impedance testing while the IMD is operating in the EMI-safe mode.

4. The method of claim 2, further comprising:
enabling a demand pacing mode while the IMD is not operating in the EMI-safe mode; and
disabling the demand pacing mode while the IMD is operating in the EMI-safe mode.

5. The method of claim 1, further comprising:
receiving, from an external device, a command that instructs the IMD to switch into the EMI-safe mode,
wherein operating the IMD in the EMI-safe mode comprises operating the IMD in the EMI-safe mode in response to receiving the command.

6. The method of claim 1, further comprising:
determining that the IMD is being subjected to EMI having one or more particular characteristics based on sensing information provided by one or more sensors, wherein operating the IMD in the EMI-safe mode comprises operating the IMD in the EMI-safe mode in response to determining that the IMD is being subjected to the EMI having the one or more particular characteristics.

7. The method of claim 1, wherein the EMI-safe mode is a magnetic resonance imaging (MRI)-safe mode.

8. The method of claim 1, further comprising:
discharging the coupling capacitor after delivering the pacing pulse;
prior to delivery of a subsequent pacing pulse via the one or more electrodes along the same pacing circuit path, discharging the coupling capacitor at a time that is closer to delivery of the subsequent pacing pulse than the time of delivery of the pacing pulse, the subsequent pacing pulse being a next sequential pacing pulse that occurs after the pacing pulse; and
delivering the subsequent pacing pulse via the one or more electrodes along the same pacing circuit path.

9. The method of claim 1, wherein delivering the pacing pulse comprises:
unconditionally delivering the pacing pulse as a next sequential step after discharging the coupling capacitor.

10. The method of claim 1, further comprising:
operating the IMD in a normal mode;
while operating the IMD in the normal mode:
avoiding, prior to the delivery of the pacing pulse, the discharge of the coupling capacitor in the pacing path at the time that is closer to the delivery of the pacing pulse than the time of the delivery of the previous pacing pulse.

11. The method of claim 1, wherein discharging the coupling capacitor comprises discharging the coupling capacitor in the pacing circuit path immediately prior to delivery of the pacing pulse.

12. The method of claim 1, further comprising:
determining whether an event that triggers the delivery of the pacing pulse has occurred,
wherein discharging the coupling capacitor comprises discharging, in response to determining that the event has occurred and prior to delivery of the pacing pulse, the coupling capacitor.

13. An implantable medical device (IMD) comprising:
a pacing output module comprising a coupling capacitor in a pacing circuit path;
a control module configured to:
operate the IMD in an electromagnetic interface (EMI)-safe mode;
while the IMD is operating in the EMI-safe mode, enable a pre-stimulation passive recharge pacing mode for the IMD;
while the IMD is operating in the EMI-safe mode and while in the pre-stimulation passive recharge pacing mode, prior to delivery of a pacing pulse via one or more electrodes along the pacing circuit path, cause the pacing output module to discharge the coupling capacitor in the pacing circuit path at a time that is closer to delivery of the pacing pulse than a time of delivery of a previous pacing pulse via the one or more electrodes along the same pacing circuit path; and
while the IMD is operating in the EMI-safe mode and while in the pre-stimulation passive recharge pacing mode, cause the pacing output module to deliver the pacing pulse via the one or more electrodes along the same pacing circuit path after discharging the coupling capacitor.

14. The device of claim 13, wherein the control module is further configured to disable the pre-stimulation passive recharge pacing mode while the IMD is not operating in the EMI-safe mode.

15. The device of claim 14, wherein the control module is further configured to enable lead impedance testing while the IMD is not operating in the EMI-safe mode, and disable lead impedance testing while the IMD is operating in the EMI-safe mode.

16. The device of claim 14, wherein the control module is further configured to enable a demand pacing mode while the IMD is not operating in the EMI-safe mode, and disable the demand pacing mode while the IMD is operating in the EMI-safe mode.

17. The device of claim 14, wherein the control module is further configured to receive, from an external device, a command that instructs the IMD to switch into the EMI-safe mode, and configured to operate the IMD in the EMI-safe mode in response to receiving the command.

18. The device of claim 14, further comprising:
one or more sensors,
wherein the control module is configured to determine that the IMD is being subjected to EMI having one or more particular characteristics based on sensing information provided by the one or more sensors, and configured to operate the IMD in the EMI-safe mode in response to determining that the IMD is being subjected to the EMI having the one or more particular characteristics.

19. The device of claim 13, wherein the EMI-safe mode is a magnetic resonance imaging (MRI)-safe mode.

20. The device of claim 13, wherein the control module is configured to cause the pacing output module to discharge the coupling capacitor after delivering the pacing pulse, configured to cause the pacing output module to discharge the coupling capacitor prior to delivery of a subsequent pacing pulse via the one or more electrodes along the same pacing circuit path, at a time that is closer to delivery of the subsequent pacing pulse than the time of delivery of the pacing pulse, the subsequent pacing pulse being a next sequential pacing pulse that occurs after the pacing pulse, and configured to cause the pacing output module to deliver the subsequent pacing pulse via the one or more electrodes along the same pacing circuit path.

21. The device of claim 13, wherein the control module is configured to cause the pacing output module to unconditionally deliver the pacing pulse as a next sequential step after discharging the coupling capacitor.

22. The device of claim 13, wherein the control module is configured to:
operate the IMD in a normal mode; and
while operating the IMD in the normal mode, cause the pacing output module to avoid, prior to the delivery of the pacing pulse, the discharge of the coupling capacitor in the pacing path at the time that is closer to the delivery of the pacing pulse than the time of the delivery of the previous pulse.

23. The device of claim 13, wherein the control module is configured to cause the pacing output module to discharge the coupling capacitor in the pacing circuit path immediately prior to delivery of the pacing pulse.

24. The device of claim 13, wherein the control module is configured to determine whether an event that triggers the delivery of the pacing pulse has occurred, and cause the pacing output module to discharge, in response to determining that the event has occurred and prior to delivery of the pacing pulse, the coupling capacitor.

25. An implantable medical device (IMD) comprising:
means for operating the IMD in an electromagnetic interference (EMI)-safe mode;
means for enabling a pre-stimulation passive recharge pacing mode for the IMD;
means for discharging a coupling capacitor in a pacing circuit path, while operating in the pre-stimulation passive recharge pacing mode and prior to delivery of a pacing pulse via one or more electrodes along the pacing circuit path, at a time that is closer to delivery of the pacing pulse than a time of delivery of a previous pacing pulse via the one or more electrodes along the same pacing circuit path; and
means for delivering the pacing pulse via the one or more electrodes along the same pacing circuit path after discharging the coupling capacitor.

26. An implantable medical device (IMD) comprising:
a stimulation output module comprising a coupling capacitor in a stimulation circuit path; and
a control module configured to:
operate the IMD in an electromagnetic interface (EMI)-safe mode;
while the IMD is operating in the EMI-safe mode, enable a pre-stimulation passive recharge mode for the IMD;
while the IMD is operating in the EMI-safe mode and while in the pre-stimulation passive recharge mode, prior to delivery of a stimulation pulse via one or more electrodes along the stimulation circuit path, cause the stimulation output module to discharge the coupling capacitor in the stimulation circuit path at a time that is closer to delivery of the stimulation pulse than a time of delivery of a previous stimulation pulse via the one or more electrodes along the same stimulation circuit path; and
while the IMD is operating in the EMI-safe mode and while in the pre-stimulation passive recharge stimulation mode, cause the stimulation output module to deliver the stimulation pulse via the one or more electrodes along the same stimulation circuit path after discharging the coupling capacitor.

* * * * *